（12）United States Patent
Chi Sing et al.

(10) Patent No.: US 9,883,919 B2
(45) Date of Patent: Feb. 6, 2018

(54) BRACHYTHERAPY APPARATUS, SYSTEMS, AND METHODS FOR USING THEM

(75) Inventors: Eduardo Chi Sing, Dana Point, CA (US); Tommy G. Nguyen, Irvine, CA (US)

(73) Assignee: CIANNA MEDICAL, INC., Aliso Viejo, CA (US)

( * ) Notice: Subject to any disclaimer, the term of this patent is extended or adjusted under 35 U.S.C. 154(b) by 1905 days.

(21) Appl. No.: 12/841,111

(22) Filed: Jul. 21, 2010

(65) Prior Publication Data

US 2012/0022314 A1   Jan. 26, 2012

(51) Int. Cl.
| | |
|---|---|
| *A61M 36/04* | (2006.01) |
| *A61B 90/00* | (2016.01) |
| *A61N 5/10* | (2006.01) |
| *A61M 25/01* | (2006.01) |

(52) U.S. Cl.
CPC ............ *A61B 90/39* (2016.02); *A61N 5/1027* (2013.01); *A61B 2090/3925* (2016.02); *A61M 25/0108* (2013.01)

(58) Field of Classification Search
CPC .. A61N 5/1002; A61N 5/1007; A61N 5/1014; A61N 5/1016
USPC ........ 600/1–8, 424, 426, 439; 604/57, 93.01
See application file for complete search history.

(56) References Cited

U.S. PATENT DOCUMENTS

| | | |
|---|---|---|
| 3,060,924 A | 10/1962 | Rush |
| 3,750,653 A | 8/1973 | Simon |
| 3,968,803 A | 7/1976 | Hyman |
| 4,427,005 A | 1/1984 | Tener |
| 4,580,561 A | 4/1986 | Williamson |
| 4,706,652 A | 11/1987 | Horowitz |
| 4,714,074 A | 12/1987 | Rey et al. |
| 4,798,212 A | 1/1989 | Arana |
| 4,936,823 A | 6/1990 | Colvin et al. |
| 4,957,476 A | 9/1990 | Cano |
| 4,976,680 A | 12/1990 | Hayman et al. |
| 5,056,523 A | 10/1991 | Hotchkiss, Jr. et al. |
| 5,106,360 A | 4/1992 | Ishiwara et al. |
| 5,152,741 A | 10/1992 | Farnio |
| 5,235,966 A | 8/1993 | Jamner |
| 5,242,372 A | 9/1993 | Carol |
| 5,279,565 A | 1/1994 | Klein et al. |
| 5,302,168 A | 4/1994 | Hess |

(Continued)

*Primary Examiner* — Samuel Gilbert

(57) ABSTRACT

A brachytherapy treatment apparatus is provided that includes a center catheter including proximal and distal ends defining a central longitudinal axis therebetween, the center catheter including a bend between the proximal and distal ends. The apparatus includes a pair of expandable catheters including pathways extending between the proximal and distal ends thereof, the expandable catheter distal ends coupled to the distal end of the core member. An actuator is coupled to the expandable catheters adjacent expandable portions that is movable relative to the center catheter for moving the expandable portions between a collapsed configuration wherein the expandable portions extend substantially parallel to the center catheter and an expanded configuration wherein the expandable portions bow away from one another substantially within a curved plane aligned generally with a bend of to the center catheter. A balloon is provided adjacent the expandable portions and surrounding a portion of the catheters.

24 Claims, 12 Drawing Sheets

(56) References Cited

U.S. PATENT DOCUMENTS

| | | |
|---|---|---|
| 5,336,178 A | 8/1994 | Kaplan et al. |
| 5,354,257 A | 10/1994 | Roubin et al. |
| 5,411,466 A | 5/1995 | Hess |
| 5,423,747 A | 6/1995 | Amano |
| 5,429,582 A | 7/1995 | Williams |
| 5,429,605 A | 7/1995 | Richling et al. |
| 5,484,384 A | 1/1996 | Fearnot |
| 5,503,613 A | 4/1996 | Weinberger |
| 5,509,900 A | 4/1996 | Kirkman |
| 5,538,502 A | 7/1996 | Johnstone |
| 5,540,659 A | 7/1996 | Teirstein |
| 5,611,767 A | 3/1997 | Williams |
| 5,653,683 A | 8/1997 | D'Andrea |
| 5,678,572 A | 10/1997 | Shaw et al. |
| 5,707,332 A | 1/1998 | Weinberger |
| 5,713,828 A | 2/1998 | Coniglione |
| 5,720,717 A | 2/1998 | D'Andrea |
| 5,730,698 A | 3/1998 | Fischell et al. |
| 5,782,740 A | 7/1998 | Schneiderman |
| 5,840,008 A | 11/1998 | Klein et al. |
| 5,843,163 A | 12/1998 | Wall |
| 5,851,171 A | 12/1998 | Gasson |
| 5,863,284 A | 1/1999 | Klein |
| 5,882,291 A | 3/1999 | Bradshaw et al. |
| 5,891,091 A | 4/1999 | Teirstein |
| 5,910,102 A | 6/1999 | Hastings |
| 5,913,813 A | 6/1999 | Williams et al. |
| 5,916,143 A | 6/1999 | Apple et al. |
| 5,931,774 A | 8/1999 | Williams et al. |
| 5,938,582 A | 8/1999 | Ciamacco, Jr. et al. |
| 5,942,209 A | 8/1999 | Leavitt et al. |
| 5,976,106 A | 11/1999 | Verin et al. |
| 6,013,019 A | 1/2000 | Fischell et al. |
| 6,022,308 A | 2/2000 | Williams |
| 6,030,333 A | 2/2000 | Sioshansi et al. |
| 6,033,357 A | 3/2000 | Ciezki et al. |
| 6,036,632 A | 3/2000 | Whitmore et al. |
| 6,056,722 A | 5/2000 | Jayaraman |
| 6,059,752 A | 5/2000 | Segal |
| 6,071,263 A | 6/2000 | Kirkman |
| 6,074,339 A | 6/2000 | Ganbale et al. |
| 6,083,148 A | 7/2000 | Williams |
| 6,117,064 A | 9/2000 | Apple et al. |
| 6,159,139 A | 12/2000 | Chiu |
| 6,159,141 A | 12/2000 | Apple et al. |
| 6,176,821 B1 | 1/2001 | Crocker et al. |
| 6,179,766 B1 | 1/2001 | Dickerson |
| 6,196,996 B1 | 3/2001 | Teirstein |
| 6,200,256 B1 | 3/2001 | Weinberger |
| 6,200,257 B1 | 3/2001 | Winkler |
| 6,213,976 B1 | 4/2001 | Trerotola |
| 6,217,585 B1 | 4/2001 | Houser et al. |
| 6,221,003 B1 | 4/2001 | Sierocuk et al. |
| 6,221,030 B1 | 4/2001 | Avaltroni |
| 6,234,951 B1 | 5/2001 | Hastings |
| 6,238,374 B1 | 5/2001 | Winkler |
| 6,258,099 B1 | 7/2001 | Mareiro et al. |
| 6,261,320 B1 | 7/2001 | Tam et al. |
| 6,264,599 B1 | 7/2001 | Slater et al. |
| 6,264,631 B1 | 7/2001 | Willis et al. |
| 6,267,775 B1 | 7/2001 | Clerc et al. |
| 6,287,249 B1 | 9/2001 | Tam et al. |
| 6,338,709 B1 | 1/2002 | Geoffrion |
| 6,358,195 B1 | 3/2002 | Green et al. |
| 6,371,904 B1 | 4/2002 | Sirimanne et al. |
| 6,413,204 B1 | 7/2002 | Winkler et al. |
| 6,458,069 B1 | 10/2002 | Tam et al. |
| 6,482,142 B1 | 11/2002 | Winkler et al. |
| 6,482,178 B1 | 11/2002 | Andrews et al. |
| 6,494,824 B1 | 12/2002 | Apple et al. |
| 6,506,145 B1 | 1/2003 | Bradshaw et al. |
| 6,508,784 B1 | 1/2003 | Shu |
| 6,527,692 B1 | 3/2003 | Weinberger |
| 6,527,693 B2 | 3/2003 | Munro, III et al. |
| 6,537,194 B1 | 3/2003 | Winkler |
| 6,540,656 B2 | 4/2003 | Fontayne et al. |
| 6,540,734 B1 | 4/2003 | Chiu et al. |
| 6,554,757 B1 | 4/2003 | Geitz |
| 6,582,353 B1 | 6/2003 | Hastings et al. |
| 6,589,158 B2 | 7/2003 | Winkler |
| 6,592,548 B2 | 7/2003 | Munro, III et al. |
| 6,607,476 B1 | 8/2003 | Barnhart |
| 6,607,478 B2 | 8/2003 | Williams |
| 6,638,206 B2 | 10/2003 | Green et al. |
| 6,641,518 B2 | 11/2003 | Wolfson et al. |
| 6,645,135 B1 | 11/2003 | Bhat |
| 6,648,811 B2 | 11/2003 | Sierocuk et al. |
| 6,659,933 B2 | 12/2003 | Asano |
| 6,673,006 B2 | 1/2004 | Winkler |
| 6,676,667 B2 | 1/2004 | Mareiro et al. |
| 6,685,619 B2 | 2/2004 | Halpern et al. |
| 6,692,460 B1 | 2/2004 | Jayaraman |
| 6,699,170 B1 | 3/2004 | Crocker et al. |
| 6,746,465 B2 | 6/2004 | Diederich et al. |
| 6,752,752 B2 | 6/2004 | Geitz |
| 6,910,999 B2 | 6/2005 | Chin et al. |
| 6,923,754 B2 | 8/2005 | Lubock |
| 6,955,641 B2 | 10/2005 | Lubock |
| 7,041,047 B2 | 5/2006 | Gellman et al. |
| 7,056,276 B2 | 6/2006 | Nakano et al. |
| 7,357,770 B1 | 4/2008 | Cutrer et al. |
| 7,413,539 B2 | 8/2008 | Lubock |
| 7,465,268 B2 | 12/2008 | Lubock |
| 2001/0007071 A1 | 7/2001 | Koblish |
| 2002/0022781 A1 | 1/2002 | McIntire |
| 2002/0016583 A1 | 2/2002 | Cragg |
| 2002/0032359 A1 | 3/2002 | Geoffrion et al. |
| 2002/0165427 A1 | 11/2002 | Yachia et al. |
| 2003/0092957 A1 | 5/2003 | Scott et al. |
| 2003/0114878 A1 | 6/2003 | Diederich et al. |
| 2003/0158515 A1 | 8/2003 | Gonzalez et al. |
| 2003/0163017 A1 | 8/2003 | Tam et al. |
| 2003/0199747 A1* | 10/2003 | Michlitsch et al. .......... 600/407 |
| 2003/0236455 A1 | 12/2003 | Cespedes et al. |
| 2004/0006305 A1 | 1/2004 | Hebert et al. |
| 2004/0068231 A1 | 4/2004 | Blondeau |
| 2004/0087828 A1 | 5/2004 | Green et al. |
| 2004/0116767 A1 | 6/2004 | Lebovic et al. |
| 2004/0127765 A1 | 7/2004 | Seiler et al. |
| 2004/0260142 A1 | 12/2004 | Lovoi |
| 2005/0061533 A1 | 3/2005 | Lovoi et al. |
| 2005/0075662 A1 | 4/2005 | Pedersen et al. |
| 2005/0080313 A1 | 4/2005 | Stewart et al. |
| 2005/0090845 A1 | 4/2005 | Boyd |
| 2005/0096647 A1 | 5/2005 | Steinke et al. |
| 2005/0101823 A1 | 5/2005 | Linares et al. |
| 2005/0101860 A1 | 5/2005 | Patrick et al. |
| 2005/0124843 A1 | 6/2005 | Singh |
| 2005/0182286 A1 | 8/2005 | Lubock |
| 2005/0240074 A1 | 10/2005 | Lubock |
| 2006/0015166 A1 | 1/2006 | Kindlein et al. |
| 2006/0020156 A1 | 1/2006 | Shukla |
| 2006/0094923 A1 | 5/2006 | Mate |
| 2006/0100475 A1 | 5/2006 | White |
| 2006/0116546 A1 | 6/2006 | Eng |
| 2006/0173233 A1 | 8/2006 | Lovoi |
| 2006/0173235 A1 | 8/2006 | Lim et al. |
| 2006/0184192 A1 | 8/2006 | Markworth et al. |
| 2006/0199990 A1 | 9/2006 | Rioux et al. |
| 2006/0235365 A1 | 10/2006 | Terwilliger et al. |
| 2006/0258895 A1 | 11/2006 | Maschke |
| 2007/0106108 A1 | 5/2007 | Hermann et al. |
| 2007/0142694 A1 | 6/2007 | Cutrer et al. |
| 2007/0167666 A1 | 7/2007 | Lubock |
| 2007/0167667 A1* | 7/2007 | Lubock et al. .................. 600/3 |
| 2007/0191668 A1 | 8/2007 | Lubock et al. |
| 2008/0091055 A1 | 4/2008 | Hermann |
| 2008/0221384 A1* | 9/2008 | Chi Sing et al. ................. 600/7 |
| 2008/0228025 A1 | 9/2008 | Quick |
| 2009/0156882 A1 | 6/2009 | Chi Sing |
| 2010/0048978 A1 | 2/2010 | Chi Sing |

\* cited by examiner

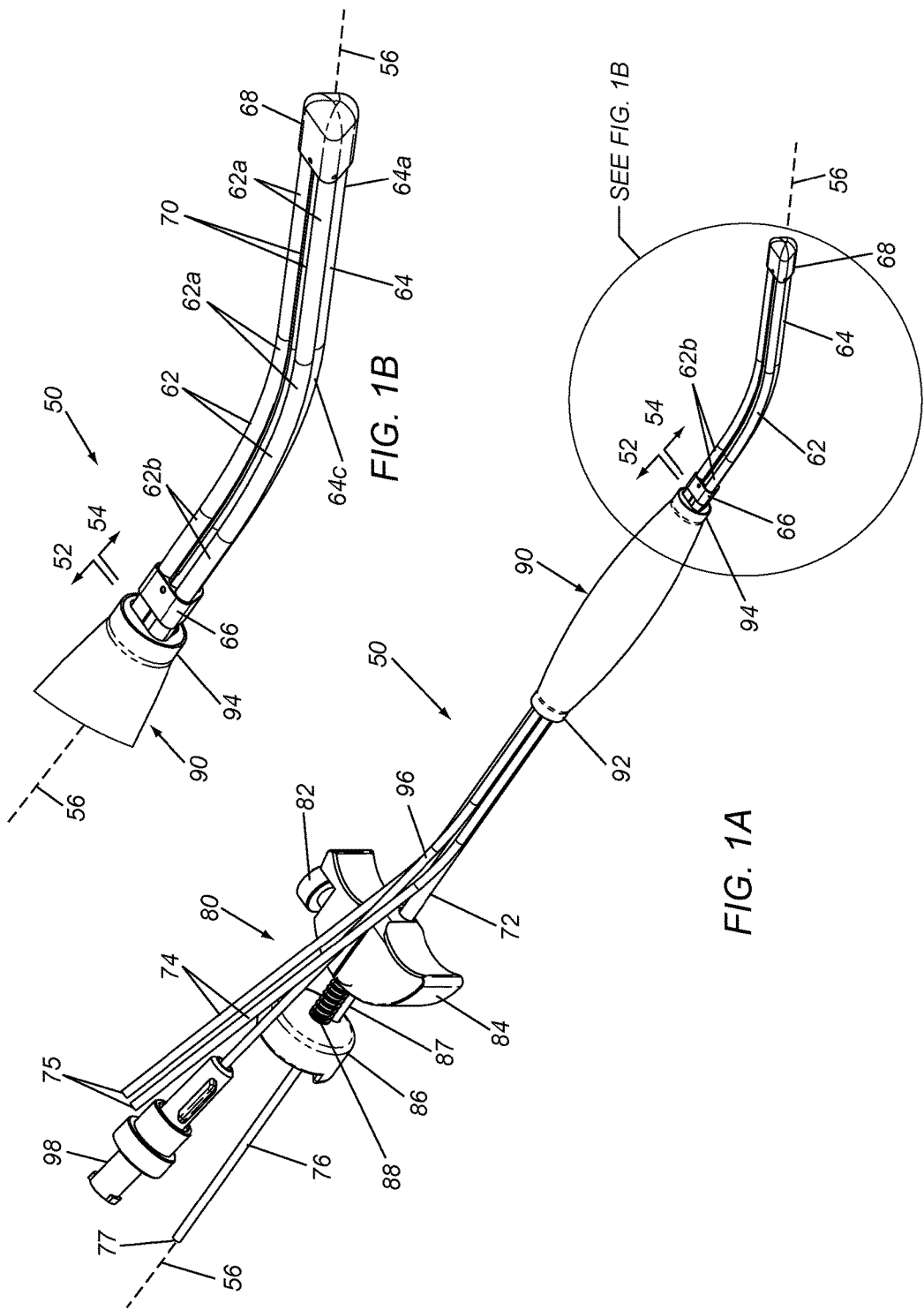

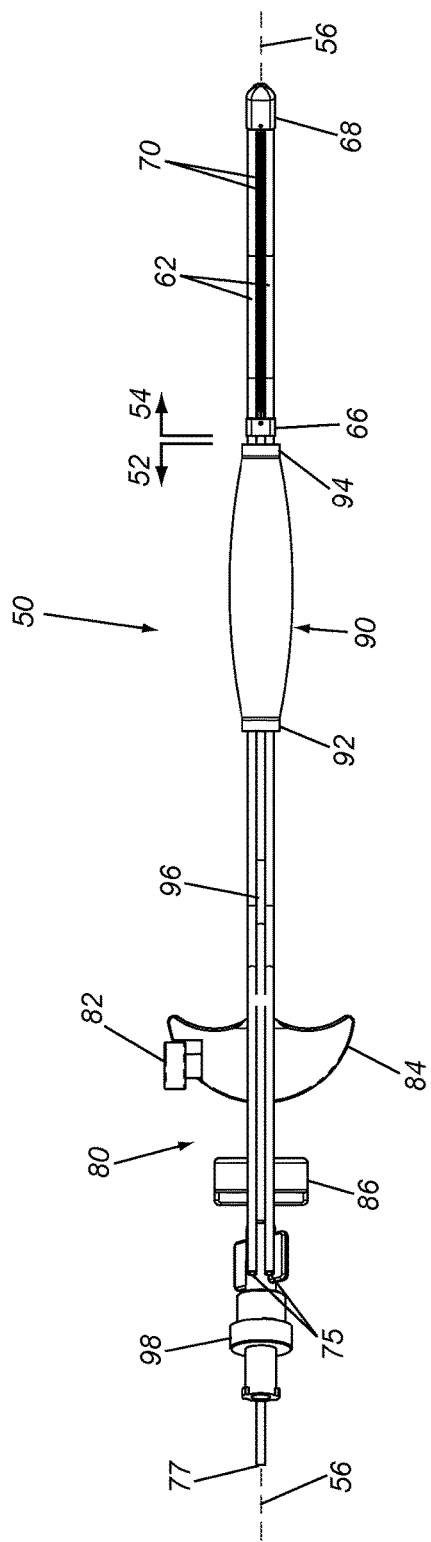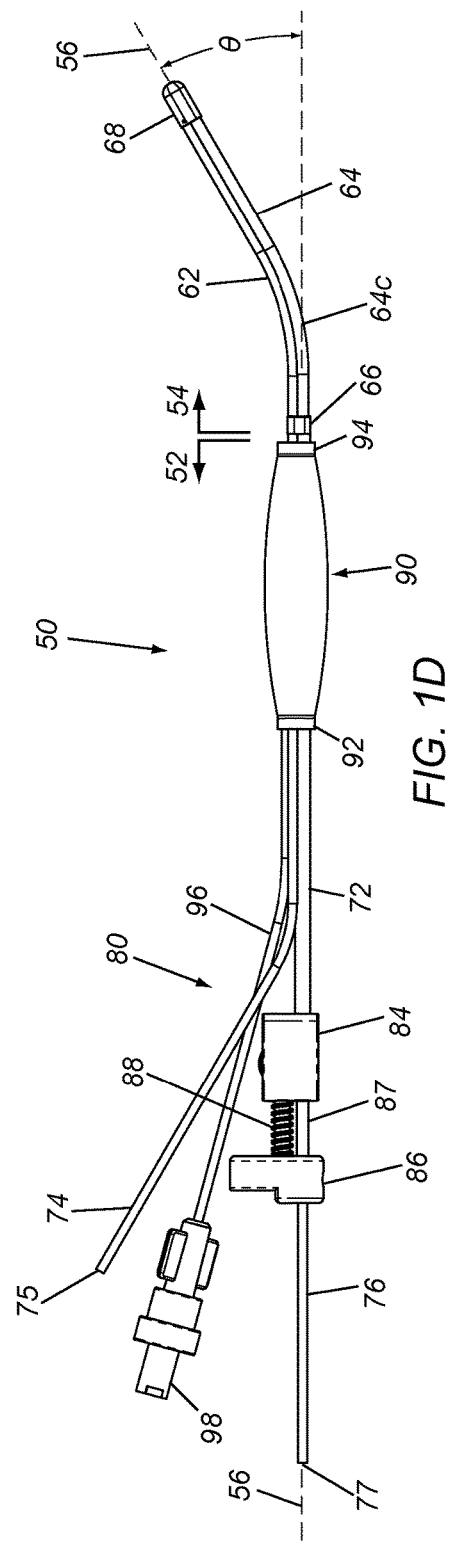
FIG. 1C
FIG. 1D

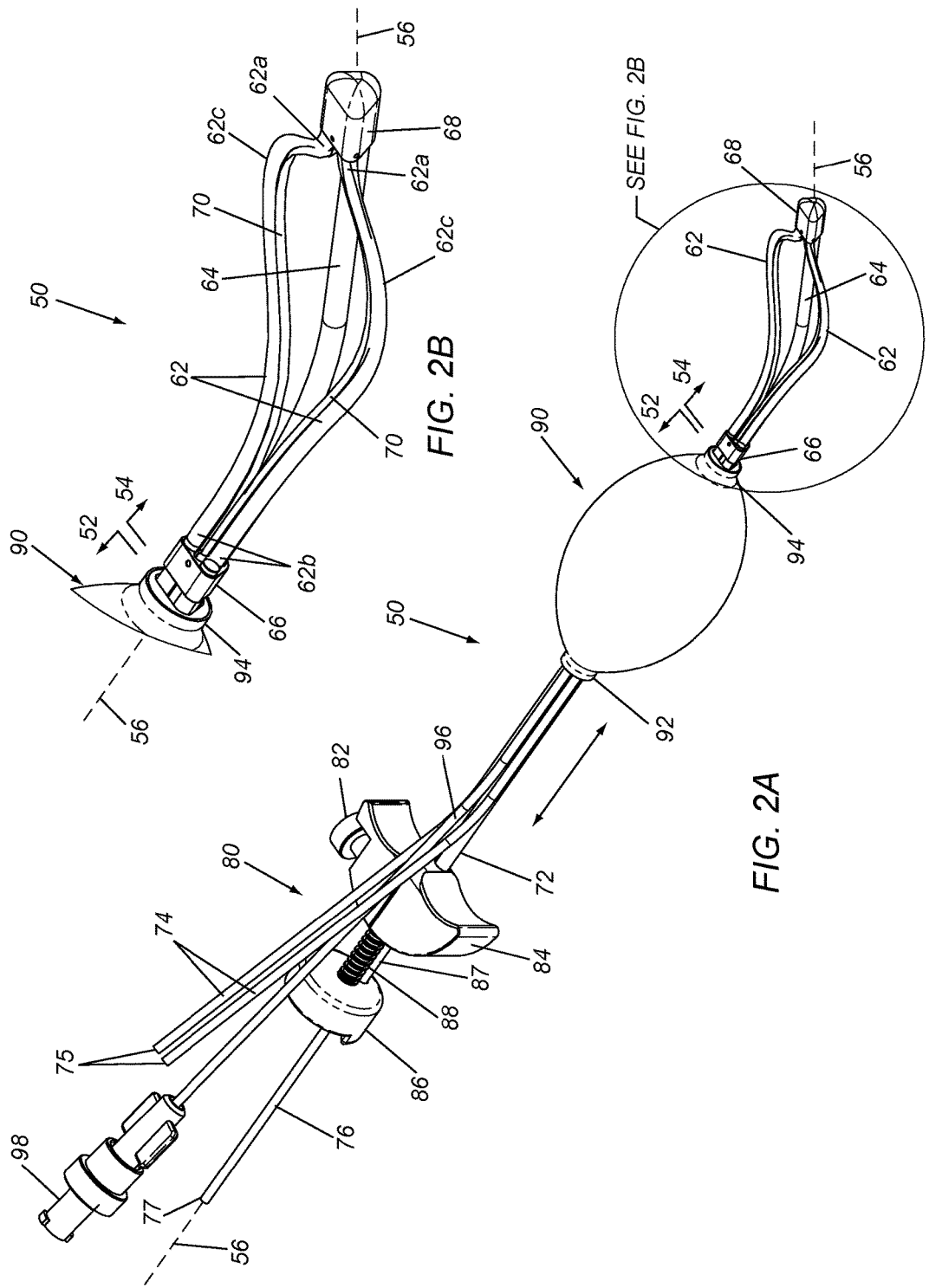

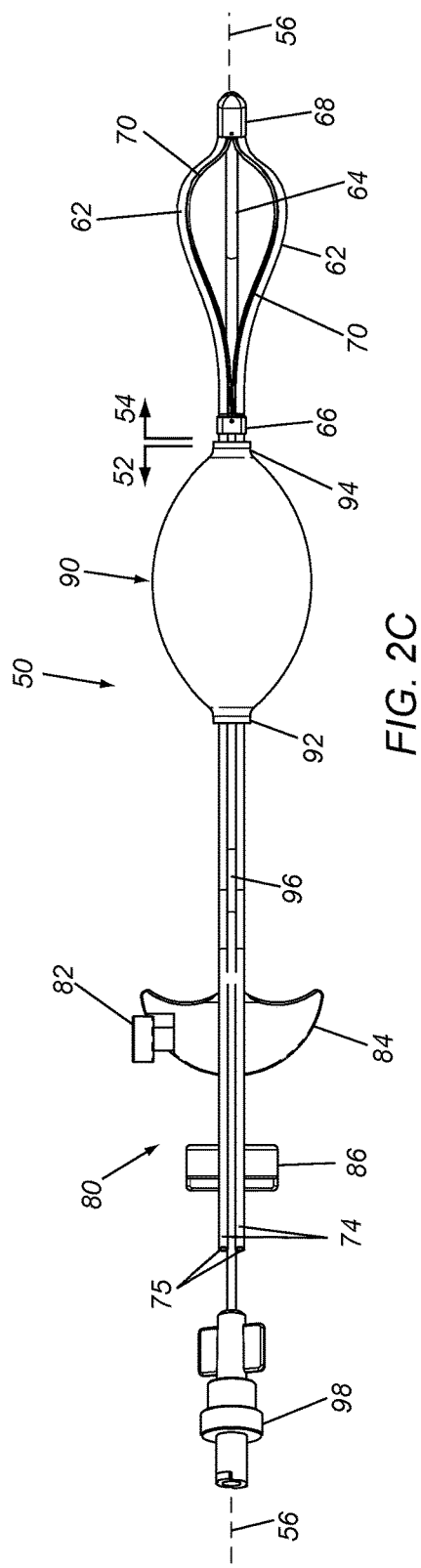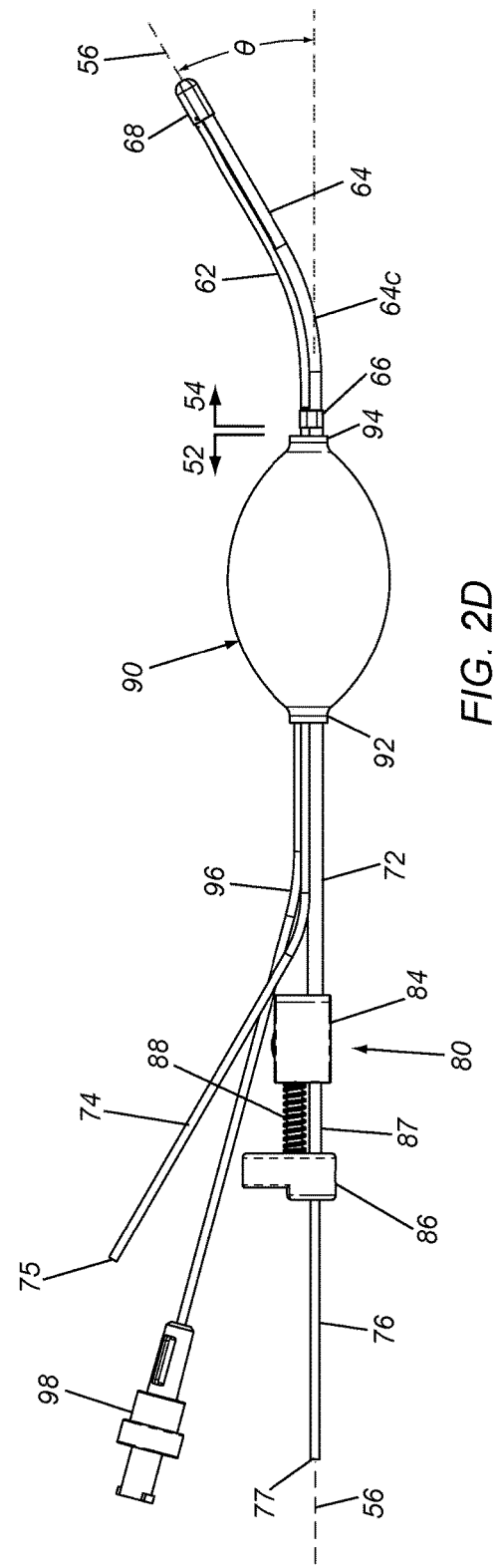
FIG. 2C
FIG. 2D

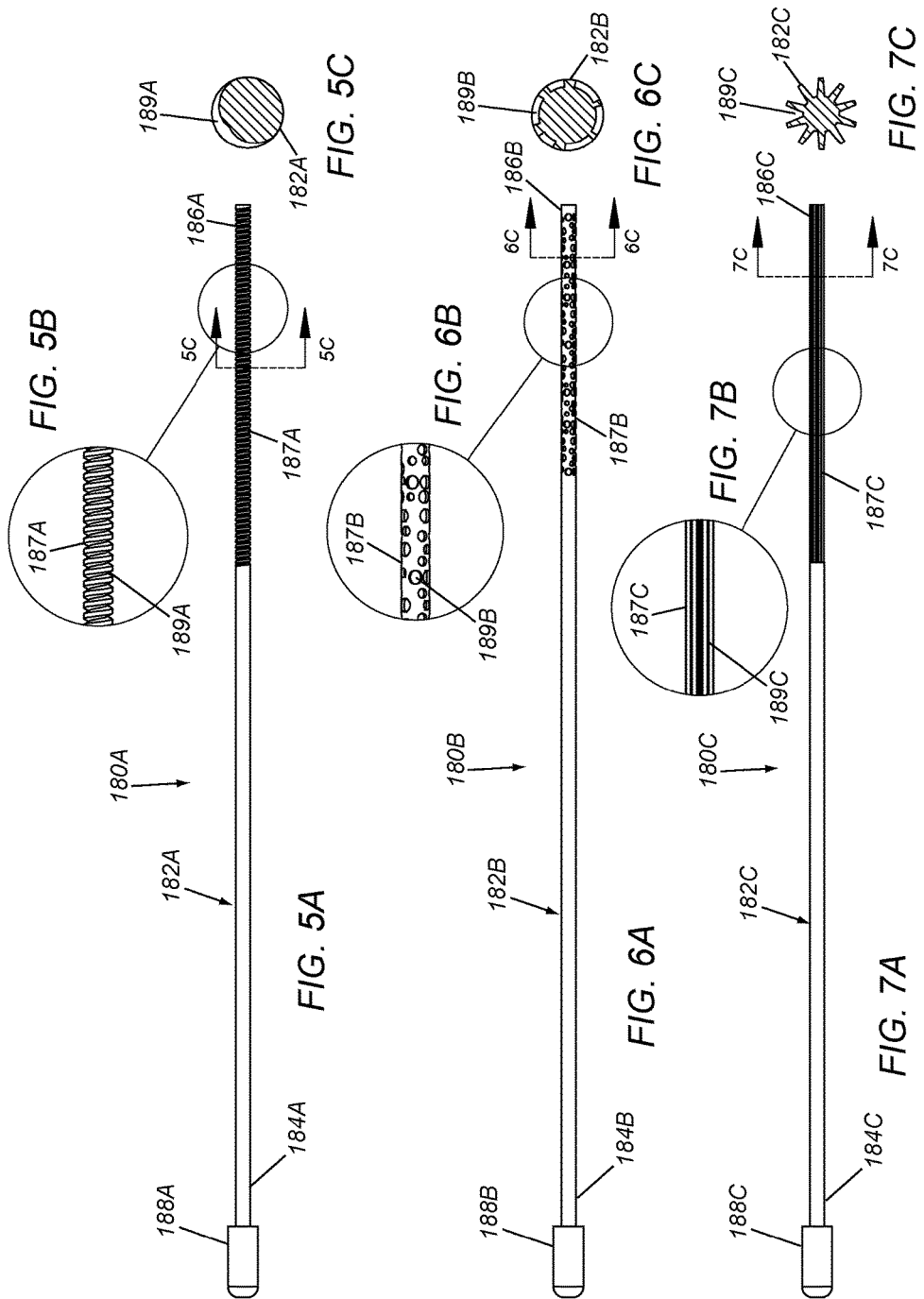

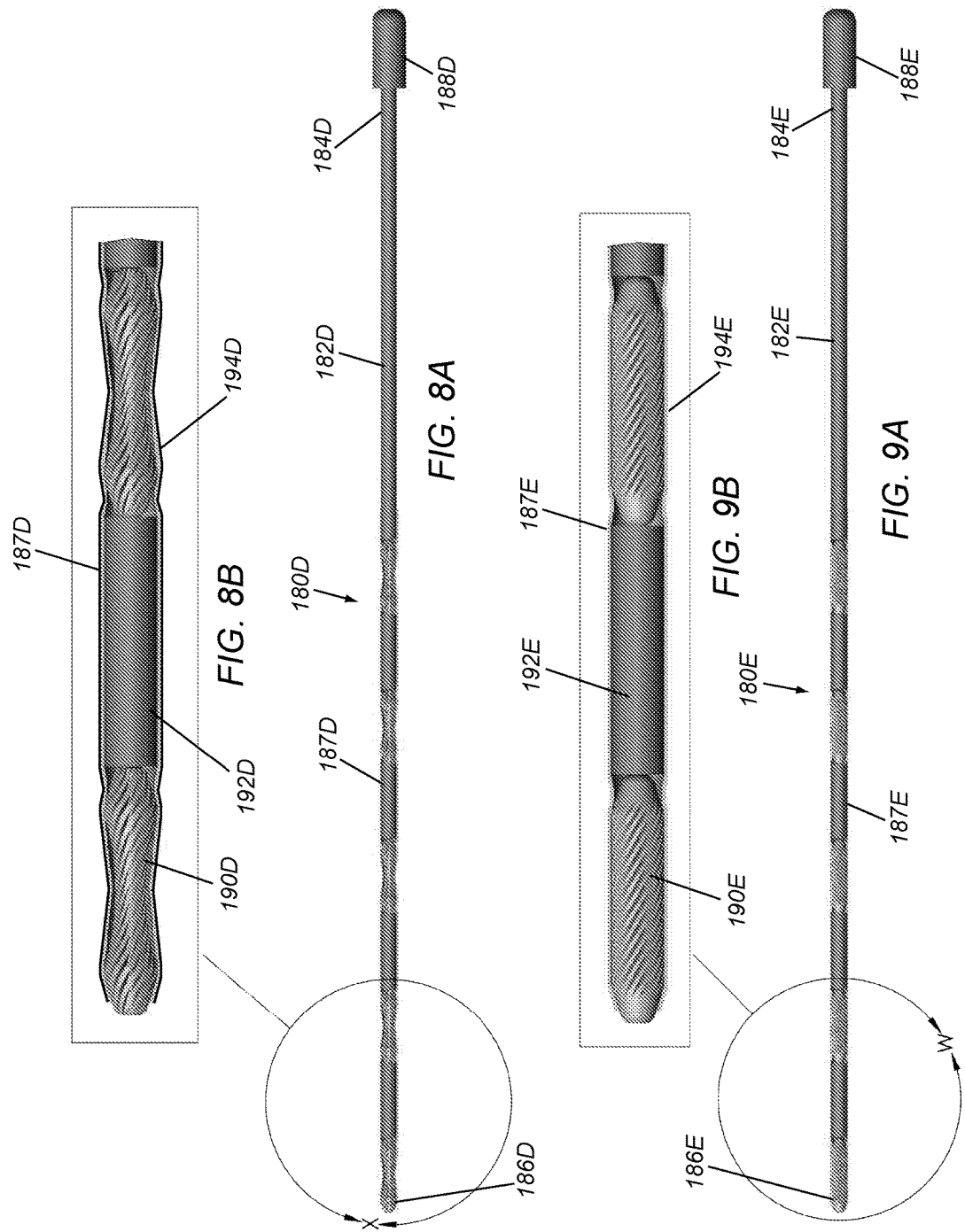

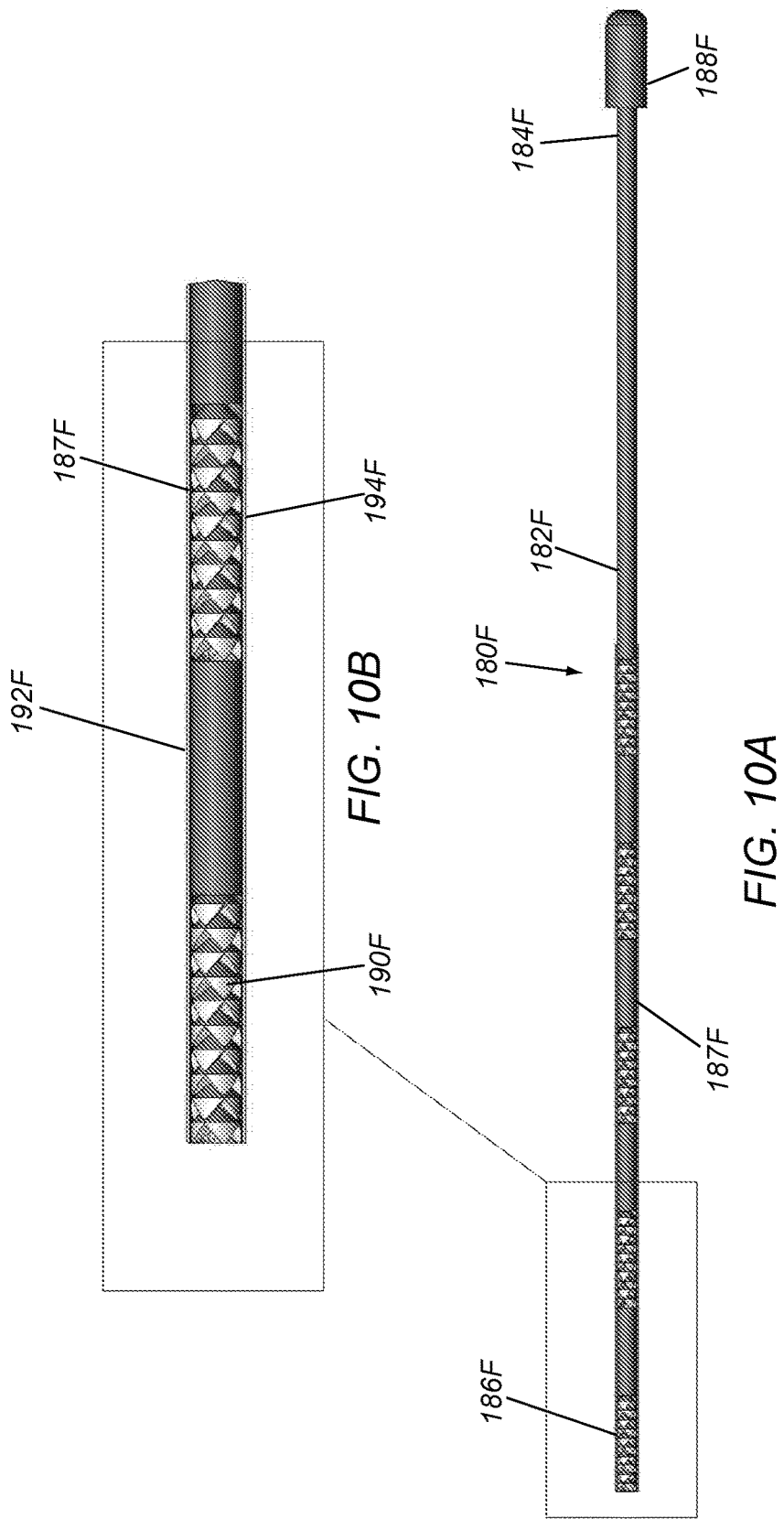

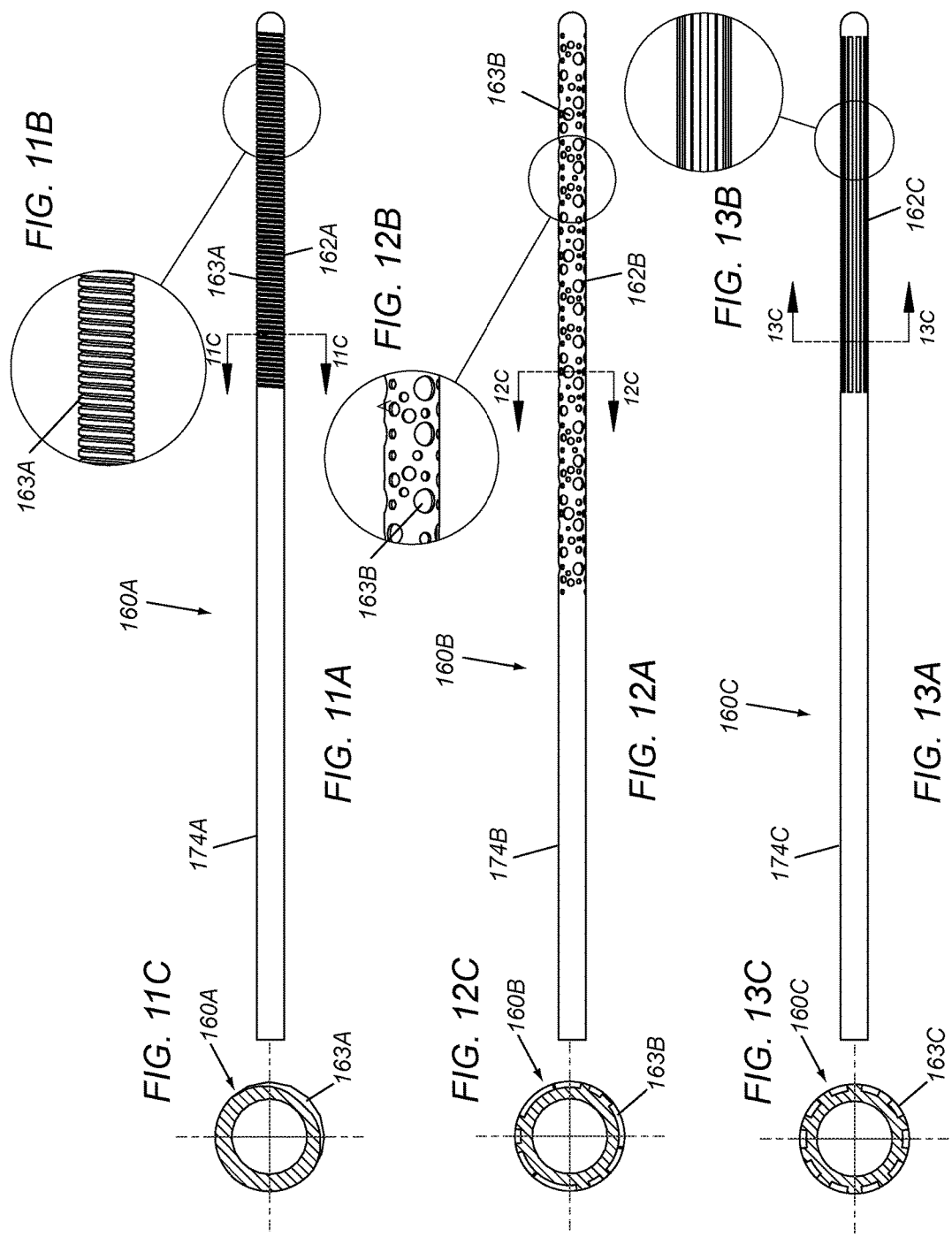

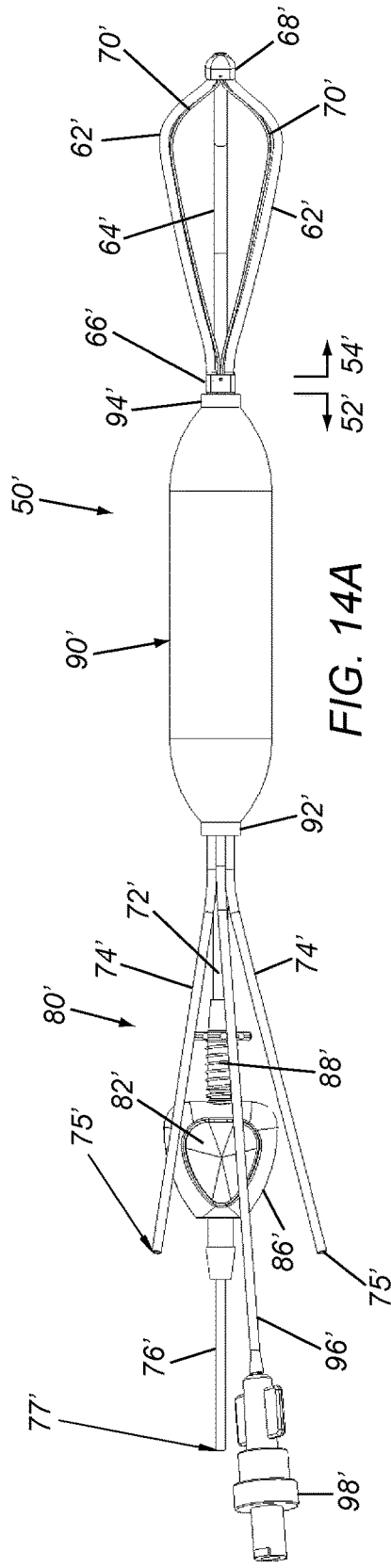
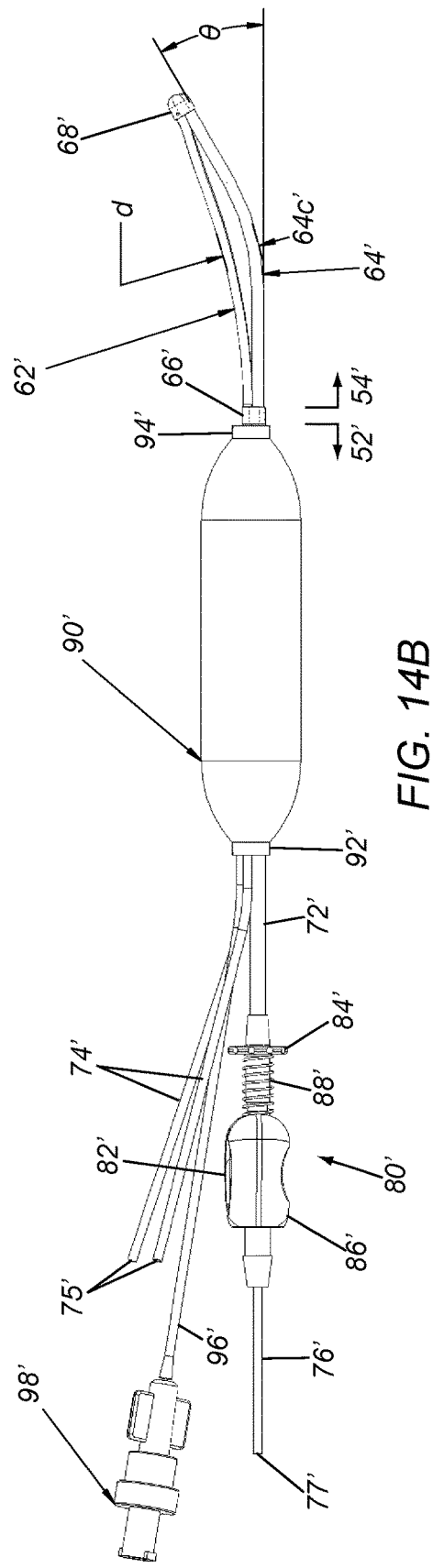
FIG. 14A
FIG. 14B

BRACHYTHERAPY APPARATUS, SYSTEMS, AND METHODS FOR USING THEM

FIELD OF THE INVENTION

The present invention relates generally to apparatus, systems, and methods for providing brachytherapy to a human or other mammalian body, and more particularly to expandable apparatus for performing brachytherapy treatment within tissue, e.g., within a body cavity, such as a vaginal cavity and/or uterine cavity, or lumpectomy cavity, and to methods for performing brachytherapy using such apparatus.

BACKGROUND

Brachytherapy is a type of radiation therapy used to treat malignant tumors, such as cancer of the breast or prostate. In general, brachytherapy involves positioning a radiation source directly into target tissue, which may include a tumor and/or tissue surrounding a cavity or void, which may contain potentially cancerous cells (such as a cavity or void created by removing a tumor).

Brachytherapy is often divided into two categories: high dose rate (HDR) and low dose rate (LDR) brachytherapy. In HDR brachytherapy, a high activity radiation source is placed into target tissue, often via a previously implanted catheter, for a short period of time, e.g., lasting from several seconds to a few minutes. In contrast, LDR brachytherapy involves placing a low activity radiation source into the target tissue for a longer, sometimes indefinite, period of time.

Both forms of brachytherapy have advantages. For instance, HDR brachytherapy provides higher radiation levels delivered over a shorter dose delivery period. LDR brachytherapy, on the other hand, utilizes lower activity radiation sources. The energy field of the LDR radiation source results in a measured and localized dose of radiation delivered to target tissue, e.g., a tumor, gland, or other tissue surrounding a cavity or void. However, the energy field thereafter decays to avoid excessive exposure of nearby healthy tissue.

Due in part to the lower activity of LDR radiation sources, LDR brachytherapy may provide various advantages. For example, for healthcare workers, exposure precautions for LDR brachytherapy may be less stringent than those for HDR brachytherapy. Also, there are radiobiological advantages of LDR brachytherapy over HDR brachytherapy (e.g., the dose rate effect), which may lead to better sparing of normal tissue during treatment. Moreover, for patients, the relatively longer implantation period associated with LDR brachytherapy may result in fewer visits to a healthcare facility over the course of radiation treatment, as compared to HDR brachytherapy where patients must return to the healthcare facility for each fraction of radiation delivered, which, for breast brachytherapy, may typically include eight to ten (8-10) fractions.

Common radiation sources used in LDR brachytherapy include radioactive isotopes such as Palladium (Pd)-103, Iodine (I)-125, Gold (Au)-198, and Iridium (Ir)-192. While the size and shape of the isotopes may vary, they may be provided in a standardized size of cylindrically shaped capsules that are approximately the size of a grain of rice, e.g., about 0.8 millimeter in diameter and about 4.5 millimeters in length, and are often referred to as "seeds."

While effective, current brachytherapy implementations have potential drawbacks. For example, LDR seeds are typically left indwelling and free floating within the target tissue and are, therefore, susceptible to migration. Moreover, once implanted, LDR seeds are generally not considered removable or repositionable. LDR brachytherapy may also require careful dose distribution calculations and seed mapping before, and often during, seed implantation. Such calculation and mapping may allow effective radiation delivery to the target tissue volume, while minimizing radiation to surrounding healthy tissue (e.g., the urethra and rectum, for example, in prostate brachytherapy). Yet, while such dose calculation and seed mapping techniques are effective, problems may exist, such as potentially significant variability in accuracy of seed placement among different clinicians.

Yet another issue with conventional LDR brachytherapy techniques is that they may require the radioactive seeds to be manipulated individually at the time of implantation, which may be a time-consuming process. Moreover, conventional LDR delivery needles are generally limited to delivering the seeds linearly (along a relatively straight line). Thus, to achieve a desired therapy profile, numerous implants (e.g., including about 50-100 seeds, as are common with prostate brachytherapy) are often required, in conjunction with potentially complex dose distribution and mapping techniques and equipment.

SUMMARY

The present invention is generally directed to apparatus, systems, and methods for delivering brachytherapy to a localized target tissue region. While potentially useful in treating most any area of the body, an exemplary application is treating cervical and/or uterine tissue, where the apparatus and systems herein may be used to place and remove a localized radiation source in an existing body cavity, e.g., a vaginal cavity and/or uterine cavity. Alternatively, the apparatus and methods may be used for treating tissue adjacent other body cavities and/or passages.

In accordance with one embodiment, a system is provided for delivering one or more therapeutic elements (e.g., radiation sources) relative to a target tissue region. Once delivered, the radiation sources may be either immediately withdrawn (e.g., in HDR applications), or left in place, e.g., implanted, for a defined period of time (e.g., in LDR applications). In either instance, the radiation sources may deliver therapy to the target tissue region in accordance with a predefined therapy profile.

In some embodiments, an access port device may be introduced into a body cavity adjacent to the target tissue region and left in place between fractions of radiation. The access port device may facilitate insertion and/or removal of therapeutic tools and may have a low profile to minimize patient discomfort.

In other embodiments, a sheath may be introduced into a passage through tissue that leads to a body cavity and left in place between fractions of treatment. The sheath may delineate and/or dilate the passage, maintain access to the body cavity, facilitate insertion and/or removal of therapeutic tools through the passage and into the body cavity, and/or have a low profile to minimize patient discomfort.

As used herein, "radiation source" and "radioactive source" may include any therapeutic element operable to deliver a dose of radiation. For example, the radiation source may be one or more radioactive seeds or, alternatively, one or more LDR or HDR wire elements (e.g., Iridium wire), e.g., as disclosed in the applications incorporated by reference elsewhere herein.

The term "implantable," as used herein, indicates the capability of a device to be inserted into the body and then maintained in a relatively fixed or static position within the surrounding tissue for an extended period of time, e.g., an hour or more and/or several hours or more, including several days or more.

Furthermore, "target tissue," "target tissue region," "target region," and "target tissue volume," as used herein, may include any portion of a human (or other mammalian) body that has been identified to benefit from radiation therapy. For example, the target tissue region may be a natural body cavity, such as the vaginal cavity and/or uterine cavity, a tumor or lesion itself, tissue proximate or surrounding the tumor, a cavity region created by tumor excision (such as the surrounding tissue or cavity associated with a lumpectomy cavity of the breast) or other surgery, and the like.

It should be noted that the apparatus, systems, and methods described herein may be used for LDR or HDR brachytherapy, as described elsewhere herein and in the applications incorporated by reference herein. Moreover, while described herein with respect to brachytherapy, the apparatus, systems, and methods may apply to other therapy regimens that benefit from the removable implantation of therapy-delivering elements. In exemplary applications, the apparatus, systems, and methods are described herein for treating cervical cancer, uterine cancer, and/or breast cancer. However, it will be appreciated that the apparatus, systems, and methods described herein may be used for treating other cancers or conditions that may benefit from brachytherapy treatment.

In accordance with one embodiment, a brachytherapy treatment apparatus is provided that includes an elongate core member; a distal tip at a distal end of the core member; an actuator moveable axially relative to the core member, at least one of the actuator and the distal tip being movable axially relative to the other of the actuator and the distal tip; and a plurality of expandable elongate members coupled to the actuator and the distal end of the core member. The expandable elongate members are movable from a collapsed configuration extending substantially parallel to the core member, to an expanded configuration when the actuator is directed distally relative to the distal tip. The elongate members include pathways for receiving a source of radiation therealong. For example, the elongate members may be tubular bodies and the pathways may be lumens extending through the tubular bodies.

In an exemplary embodiment, the core member may have a substantially fixed predetermined shape, e.g., defining a predetermined curve. In addition or alternatively, the apparatus may include an expandable member adjacent the expandable elongate members. For example, the expandable member may be a balloon located proximal to the expandable elongate members.

In another exemplary embodiment, in the expanded configuration, the expandable elongate members may form a pear shape that bulges near the distal end of the core member and tapers towards the actuator. In another exemplary embodiment, the expandable elongate members may define a planar configuration, e.g., including a pair of elongate members that expand away from one another substantially within a plane, which may be curved or substantially straight.

In still another exemplary embodiment, the plurality of expandable elongate members may be arranged asymmetrically around the core member. For example, the plurality of expandable elongate members may be disposed on one side of a plane extending substantially parallel to a longitudinal axis of the core member. More particularly, the apparatus may include two or three expandable elongate members that are disposed substantially on one side of a plane defined by a central longitudinal axis of the core member. The distal tip of the brachytherapy treatment apparatus may be configured for positioning within a cervix, e.g., having a tapered and/or extended tip shape.

Optionally, in any of these embodiments, the apparatus may include a plurality of elongate support members configured for supporting respective expandable elongate members when the elongate members are directed between the collapsed and expanded configurations. For example, the support members may be attached to the plurality of expandable elongate members for biasing the plurality of expandable elongate members to expand generally radially without substantial lateral movement.

In addition or alternatively, the apparatus may include one or more markers for enhancing imaging of the apparatus using external imaging, such as x-ray imaging, e.g., CT scan, ultrasound imaging, and the like. For example, catheter protectors and/or marker devices may be introduced into lumens of the elongate members that include one or more features to enhance imaging the apparatus. In exemplary embodiments, the features may include one or more helical grooves, circular and/or elliptical recesses, and/or longitudinal grooves formed or otherwise provided in an outer surface of the marker devices. Alternatively, such features may be provided in outer surfaces of the elongate members themselves. Optionally, the marker devices may include caps or other elements for sealing the lumens, e.g., to prevent fluid or other material from entering the lumens, e.g., between treatments during which the apparatus remains implanted within a patient's body.

In accordance with another embodiment, a brachytherapy treatment apparatus is provided that includes an elongate core member, a distal tip at a distal end of the core member, an actuator moveable axially relative to the core member, the actuator and/or distal tip being movable axially relative to one another, and a plurality of elongate members coupled to the actuator and including unattached or free distal ends that are constrained in a collapsed configuration that extends substantially parallel to the core member. The elongate members are movable between the collapsed configuration and an expanded configuration when the actuator is directed distally relative to the distal tip, e.g., such that the distal ends of the elongate members are directed transversely away from the core member. The expandable elongate members include pathways for receiving a source of radiation therealong.

In an exemplary embodiment, in the expanded configuration, the distal ends of the expandable elongate members may curve radially outwardly away from the core member. For example, support members may be carried by and/or coupled to respective elongate members for expanding the distal ends of the elongate members away from the core member as the distal ends are exposed or otherwise deployed.

Optionally, the apparatus may include a core member handle fixedly attached to the core member. The plurality of elongate members may be fixedly coupled to the actuator while the core member may be slidable within a central opening of the actuator.

In one embodiment, the apparatus may include a plurality of support members configured for supporting respective elongate members, e.g., to bias the elongate members to be deployed in a predetermined orientation when directed to the expanded configuration. The preset configuration of the support members, relative to the expanded configuration, may provide increased dose coverage to the target tissue and/or better dose sculpting capabilities, e.g., which may minimize exposure of non-targeted tissue to radiation. Also, the predetermined orientation of the support members may have an expanded "tear drop" shape, which may help to self center the apparatus when placed inside a body cavity (e.g., the uterus). For example, the support members may be attached to respective elongate members for biasing the elongate members to curve radially outwardly away from the core member upon deployment.

In accordance with another embodiment, a brachytherapy treatment apparatus is provided that includes an elongate core member including proximal and distal ends defining a central longitudinal axis therebetween, the core member including a bend between the proximal and distal ends. The apparatus includes a pair of elongate members including proximal and distal ends and pathways extending between the elongate member proximal and distal ends for receiving a source of radiation therealong, the elongate member distal ends coupled to the distal end of the core member. An actuator is coupled to the elongate members adjacent distal portions of the elongate members and movable axially relative to the core member for moving the distal portions of the elongate members between a collapsed configuration wherein the distal portions extend substantially parallel to the core member and an expanded configuration wherein the distal portions bow away from one another substantially within a curved plane offset from or extending substantially parallel to the core member. For example, in the expanded configuration, the elongate members may define a different radius of curvature than the bend of the core member, e.g., such that the elongate members and the core member provide multiple curved planes for delivering radiation to surrounding tissue.

Optionally, the apparatus also include an expandable member adjacent the distal portions and surrounding a portion of the elongate members and/or core member. For example, the expandable member may be a balloon disposed proximal to the distal portions that may stabilize the apparatus within a body cavity and/or protect surrounding tissue when one or more radiation sources are directed through the apparatus to the distal portions.

In accordance with yet another embodiment, a brachytherapy treatment apparatus is provided that includes an elongate core member including proximal and distal ends defining a central longitudinal axis therebetween, and a plurality of elongate members including proximal and distal ends and pathways extending between the elongate member proximal and distal ends for receiving a source of radiation therealong, the elongate member distal ends coupled to the distal end of the core member. An actuator may be coupled to the elongate members proximal to distal portions of the elongate members and movable axially relative to the core member for moving the distal portions of the elongate members between a collapsed configuration wherein the distal portions extend substantially parallel to the core member and an expanded configuration wherein the distal portions bow away from one another. An expandable member may be fixed to the elongate members proximal the distal portions and surrounding a portion of the elongate members.

In accordance with still another embodiment, a method is provided for brachytherapy treatment of tissue adjacent a vaginal cavity and/or uterus of a patient that includes introducing a distal portion of an applicator into the vaginal cavity with the distal portion of the applicator in a collapsed configuration. Optionally, the distal portion may include a bend contoured, e.g., to the shape of the vaginal cavity and/or uterus, for example, to facilitate advancement and/or positioning the applicator.

The distal portion of the applicator may be directed to an expanded configuration within the vaginal cavity or uterus such that pathways extending along the distal portion are directed away from a central longitudinal axis of the applicator, and one or more radiation sources may be introduced along the pathways to deliver radiation to tissue adjacent the vaginal cavity or uterus.

In accordance with yet another embodiment, a method is provided for brachytherapy treatment of tissue within a body cavity of a patient that includes introducing a distal portion of an applicator through a passage through tissue into the body cavity with the distal portion of the applicator in a collapsed configuration, the applicator including a plurality of pathways extending from outside the patient's body to the distal portion. The distal portion of the applicator may be directed to an expanded configuration within the body cavity such that the pathways are directed away from a central longitudinal axis of the applicator, and an expandable member on the applicator proximal to the distal portion may be expanded such that the expandable member engages surrounding tissue. Radiation may be delivered to a target location adjacent the body cavity via the distal portion of the applicator. The expandable member may stabilize the applicator within the body cavity and/or may protect tissue surrounding the expandable member from substantial exposure to radiation as one or more radiation sources are directed along the pathways to the distal portion of the applicator.

The above summary is not intended to describe each embodiment or every implementation of the present invention. Rather, a more complete understanding of the invention will become apparent and appreciated by reference to the following detailed description and claims in view of the accompanying drawings.

BRIEF DESCRIPTION OF THE DRAWINGS

FIG. 1A is a perspective view of an exemplary embodiment of an applicator for brachytherapy treatment in a collapsed configuration.

FIG. 1B is a detail of a distal portion of the applicator of FIG. 1A in the collapsed configuration.

FIGS. 1C and 1D are top and side views, respectively, of the applicator of FIG. 1A in the collapsed configuration.

FIG. 2A is a perspective view of the applicator of FIGS. 1A-1D in an expanded configuration.

FIG. 2B is a detail of the distal portion of the applicator of FIG. 2C in the expanded configuration.

FIGS. 2C and 2D are top and side views, respectively, of the applicator of FIG. 2A in the expanded configuration.

FIG. 5A is a side view of another exemplary embodiment of a catheter protector/marker device.

FIG. 5B is a detail of features formed on a distal portion of the marker device of FIG. 5A.

FIG. 5C is a cross-sectional view of the marker device of FIG. 5A, taken along line 5C-5C.

FIG. 6A is a side view of still another exemplary embodiment of a catheter protector/marker device.

FIG. 6B is a detail of features formed on a distal portion of the marker device of FIG. 6A.

FIG. 6C is a cross-sectional view of the marker device of FIG. 6A, taken along line 6C-6C.

FIG. 7A is a side view of yet another exemplary embodiment of a catheter protector/marker device.

FIG. 7B is a detail of features formed on a distal portion of the marker device of FIG. 7A.

FIG. 7C is a cross-sectional view of the marker device of FIG. 7A, taken along line 7C-7C.

FIG. 8A is a side view of still another exemplary embodiment of a catheter protector/marker device.

FIG. 8B is a detail of a distal portion of the marker device of FIG. 8A, including spacers between image enhancing seeds and encased in heat shrink tubing.

FIG. 9A is a side view of yet another exemplary embodiment of a catheter protector/marker device.

FIG. 9B is a detail of a distal portion of the marker device of FIG. 9A, including spacers between image enhancing seeds and encased in heat shrink tubing.

FIG. 10A is a side view of still another exemplary embodiment of a catheter protector/marker device.

FIG. 10B is a detail of a distal portion of the marker device of FIG. 10A, including spacers between image enhancing seeds and encased in heat shrink tubing.

FIG. 11A is a side view of an exemplary embodiment of a tubular body including image enhancing features that may be provided for a catheter and/or tubular extension on the applicator of FIGS. 1A-2D.

FIG. 11B is a detail of features formed on a distal portion of the tubular body of FIG. 11A.

FIG. 11C is a cross-sectional view of the tubular body of FIG. 11A, taken along line 11C-11C.

FIG. 12A is a side view of another embodiment of a tubular body including image enhancing features that may be provided for a catheter and/or tubular extension on the applicator of FIGS. 1A-2D.

FIG. 12B is a detail of features formed on a distal portion of the tubular body of FIG. 12A.

FIG. 12C is a cross-sectional view of the tubular body of FIG. 12A, taken along line 12C-12C.

FIG. 13A is a side view of yet another embodiment of a tubular body including image enhancing features that may be provided for a catheter and/or tubular extension on the applicator of FIGS. 1A-2D.

FIG. 13B is a detail of features formed on a distal portion of the tubular body of FIG. 13A.

FIG. 13C is a cross-sectional view of the tubular body of FIG. 13A, taken along line 13C-13C.

FIGS. 14A and 14B area top and side views of an alternative embodiment of the applicator of FIGS. 1A-2D in an expanded configuration.

DETAILED DESCRIPTION OF THE EXEMPLARY EMBODIMENTS

Figure 3A:
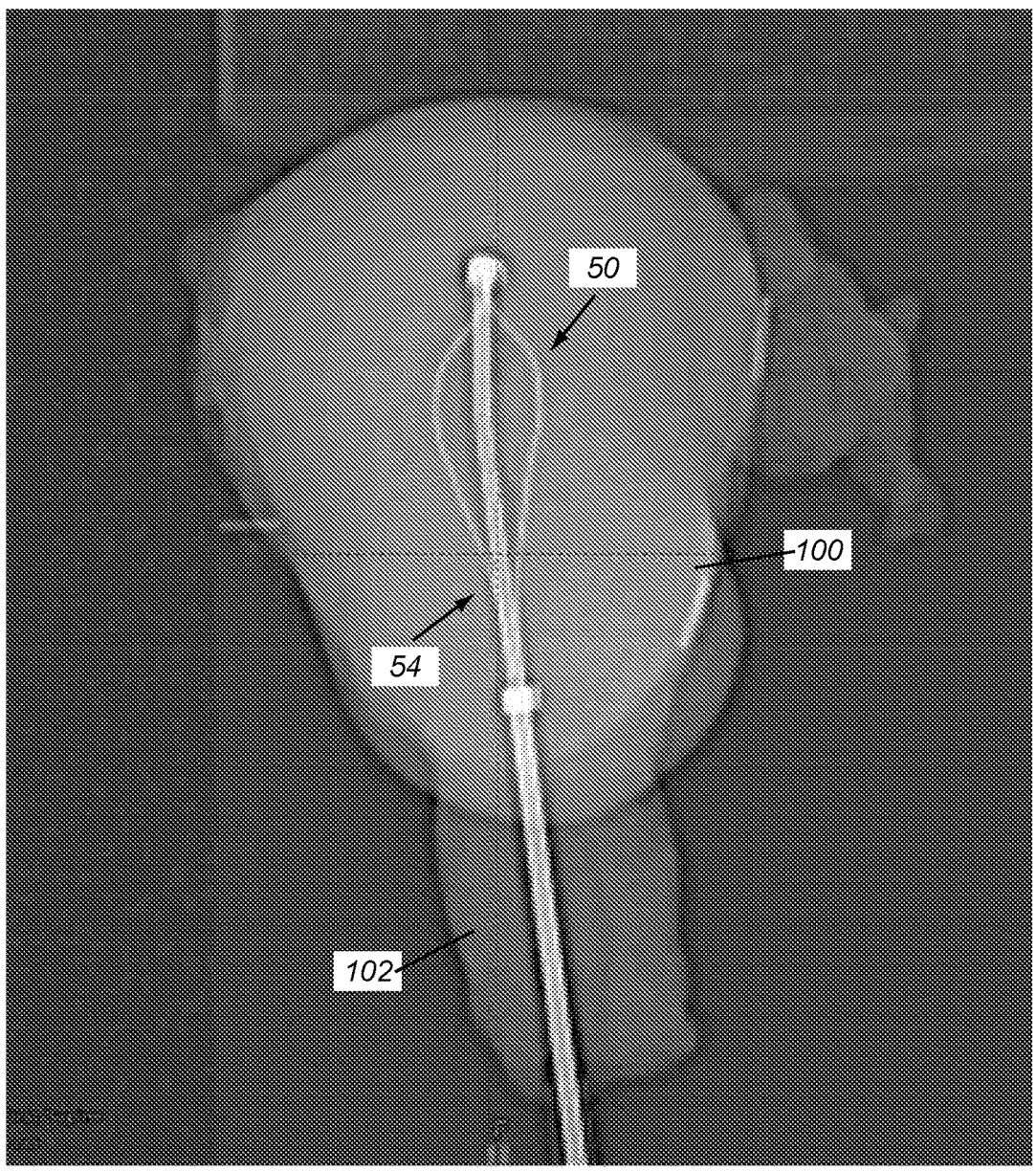
FIG. 3A is an x-ray image taken anteriorly of a patient's body showing the applicator of FIGS. 1A-2D introduced and expanded within the patient's uterus.

Turning to the drawings, FIGS. 1A-2D show an exemplary embodiment of an expandable brachytherapy applicator 50 that includes an expandable distal or therapy delivery portion 54, which may be introduced into a body cavity or other target tissue region, and a proximal or tail portion 52, which may extend from the target tissue region out of a patient's body during use, e.g., generally defining a longitudinal axis 56 therebetween. As best seen in FIGS. 1B and 2B, the distal portion 54 of the applicator 50 includes a plurality of expandable catheters 62, e.g., two catheters 62, disposed adjacent a center catheter 64 and extending between a hub 66 and a distal tip 68. As shown in FIGS. 1A and 2A, the proximal portion 52 of the applicator 50 generally includes a shaft 72 coupled to the hub 66, tubular extensions 74, 76 extending proximally from the hub 66 and communicating with respective catheters 62, 64, and an actuator 80 for operating the applicator 50. In addition, optionally, the applicator 50 may include a balloon or other expandable member 90 on the proximal portion 52, e.g., attached around the shaft 72 and/or tubular extensions 74, for positioning and/or stabilizing the applicator 50 during use, as described further below.

With particular reference to FIGS. 1B and 2B, distal ends 62a, 64a of the catheters 62, 64 may be coupled to the distal tip 68 and/or to each other, e.g., by interference fit and/or connectors (not shown) within the distal tip 68, by bonding with adhesive, sonic welding, fusing, and the like. The distal tip 62 may be sized for positioning within an os of a cervix and/or within a tip of an access device (not shown), e.g., similar to embodiments disclosed in the applications incorporated by reference herein. Proximal ends 62b of the expandable catheters 62 may be coupled to the hub 66, while the center catheter 64 may be slidable through or otherwise movable relative to the hub 66. The center catheter 64 may be actuatable from the proximal portion 52 of the applicator 50, e.g., by the actuator 80, to direct the distal end 64a of the center catheter 64, and consequently, the distal tip 68, towards or away from the hub 66.

Thus, as described further below, the center catheter 68 may be actuated to direct the distal tip 68 proximally towards the hub 66 (or the hub 66 and/or the distal tip 68 may be otherwise directed towards one another), thereby causing expandable portions 62c of the expandable catheters 62 between the hub 66 and distal tip 68 to be subjected to an axially compressive stress. This stress causes the expandable portions 62c to bow radially outwardly from a collapsed, e.g., substantially axial, configuration (shown in FIGS. 1A-1D) to an expanded, e.g., curved, configuration (shown in FIGS. 2A-2D). Conversely, the hub 66 and the distal tip 68 may be directed away from one another, e.g., by directing the center catheter 64 distally, thereby causing the expandable portions 62c to be pulled back radially inwardly from the expanded configuration towards the collapsed configuration.

As shown in FIGS. 1A-1D, in the collapsed configuration, the expandable portions 62c of the expandable catheters 62 may extend substantially parallel to the center catheter 64 and/or longitudinal axis 56. As best seen in FIGS. 2C and 2D, the expandable portions 62c may expand away from one another substantially within a curved plane, i.e. to define a substantially planar shape in the expanded configuration, e.g., that generally follows the curvature of the center catheter 64.

Alternatively, as shown in FIGS. 14A and 14B, expandable portions 62c' of expandable catheters 62' may expand to define a curved substantially planar shape that defines a different radius of curvature than the bend of the center catheter 64', e.g., such that the catheters 62', 64' provide multiple curved planes for delivering radiation to surrounding tissue, as described further below.

Returning to FIGS. 1A-1D, the center catheter 64 may be offset below the curved plane defined by the catheters 62, e.g., such that the catheters 62 are offset asymmetrically from the central axis 56 of the center catheter 64. The center catheter 64 may be substantially rigid and formed into a predetermined shape, e.g., defining a curve between the hub 66 and distal tip 68. In an exemplary embodiment, the center catheter 64 may include a fixed bend at an intermediate location 64c between the hub 66 and the distal tip 68, defining a predetermined angle θ, e.g., between about ten and sixty degrees (10-60°), e.g., about thirty degrees (30°), as shown in FIGS. 1D and 2D. Alternatively, if desired, the center catheter 64 may include a malleable section (not shown), e.g., between the hub 66 and the distal tip 68, such that the angle, bend, and/or other shape of the center catheter 64 may be adjusted as desired based upon the particular anatomy encountered during a procedure.

Optionally, as best seen in FIGS. 1B and 2B, at least the expandable portions 62c of the expandable catheters 62 may include one or more support members 70, e.g., attached to or otherwise extending at least partially along the expandable portions 62c. The support members 70 may bias the expandable portions 62c of the expandable catheters 62 to remain substantially within the desired plane during expansion and collapse with minimal lateral movement out of the plane. In an exemplary embodiment, the support members 70 may be elongate strips of material, e.g., metal, such as stainless steel or Nitinol, plastic, or composite material, that may be elastically deflected during use of the applicator 50, e.g., when the expandable catheters 62 are directed between the collapsed and expanded configurations. The support members 70 may be attached to the expandable catheters 62, e.g., by bonding with adhesive, sonic welding, overlying sleeves (not shown), and the like. Alternatively, the support members 70 may be integrally molded with the support members 70 and/or the support members 70 may be molded over or around the support members 70.

The tubular extensions 74, 76 extend proximally from the hub 66 and include lumens communicating with respective catheters 62, 64. For example, the tubular extensions 74 may be coupled to the hub 66 generally opposite the proximal ends 62b of the expandable catheters 62. Alternatively, the tubular extensions 74 may be integrally formed with the expandable catheters 62, e.g., as a single piece, for example, as shown in FIGS. 11A-13A. Similarly, the tubular extension 76 may be coupled to the center catheter 64 and/or integrally formed therewith as a single piece. Thus, one or more radiation sources (not shown) may be inserted into openings 75, 77 in the tubular extensions 74, 76 and through the respective lumens into the catheters 62, 64, where the radiation source(s) may be positioned at one or more locations, as described further below.

Optionally, if desired, the applicator 50 may include one or more additional expandable catheters (not shown). For example, the applicator 50 may include one or more expandable catheters adjacent the expandable catheters 62 generally opposite the center catheter 64, e.g., such that the one or more additional expandable catheters expand above the curved plane defined by the expandable catheters 62 when the applicator 50 is directed to the expanded configuration, e.g., similar to applicators disclosed in application Ser. No. 12/543,463, filed Aug. 18, 2009, published as U.S. Publication No. 2010/0048977 on Feb. 25, 2010, the entire disclosure of which is expressly incorporated by reference herein.

Returning to FIGS. 1A and 2A, the actuator 80 may be coupled between the center catheter 62 and the hub 66, e.g., on the proximal portion 52 of the applicator 50, for directing the expandable portions 62c of the expandable catheters 62 between the collapsed and expanded configurations. For example, as shown, the actuator 80 may include a handle 84 on the shaft 72, thereby coupling the handle 84 to the hub 66, and a plunger 86 on the tubular extension 76, thereby coupling the plunger 86 to the center catheter 64. The shaft 72 may be substantially rigid and/or axially incompressible (e.g., but bendable, if desired) such that the distance between the hub 66 and the handle 84 remains substantially fixed during use of the applicator 50. For example, the shaft 72 may be a tubular body, e.g., including a lumen (not shown) for slidably receiving the center catheter 64 and/or tubular extension 76 therethrough. Alternatively, the center catheter 76 and/or tubular extension 76 may slide or otherwise move adjacent to the shaft 72 rather than through the shaft 72.

The plunger 86 may be movable relative to the handle 84, e.g., slidable axially between a first or distal position (best seen in FIG. 1D) and a second or proximal position (best seen in FIG. 2D), to move the center catheter 64 relative to the shaft 72 and consequently relative to the expandable catheters 62. For example, as shown, the plunger 86 may include a piston or other elongate member 87 that is slidable a predetermined distance into and out of the handle 84, thereby limiting motion of the plunger 86 between the first and second positions.

Optionally, the plunger 86 may be biased to one of the first and second positions, e.g., by a spring 88 between the plunger 86 and handle 84. As shown, the spring 88 may be a compression spring located between the handle 84 and plunger 86 (e.g., on a shaft, not shown), although alternatively, the spring may be located inside the handle 84 (not shown), e.g., coupled to the piston 87. In addition or alternatively, the handle 84 may include a locking pin 82, which may be selectively engaged with the plunger 86 to selectively lock the plunger 86 in a desired position. Alternatively, as shown in FIGS. 14A and 14B, the actuator 80' may include a plunger 86' that includes a locking button or detent 82' that may be activated to secure the plunger 86' in a desired position relative to shaft 72'. For example, as shown in FIGS. 1A-2D, the locking pin 82 may create an interference fit with the piston 87 when engaged, or the locking pin 82 may be received in one or more apertures (not shown) in the piston 87 to lock the plunger 86. The locking pin 82 may thread in and out of the handle 84 or may simply slide directly into and out of the handle 84. Alternatively, it will be appreciated that other locking mechanisms may be provided between the handle 84 and plunger 86, as desired, instead of or in addition to the locking pin 82. For example, the locking button 82' shown in FIGS. 14A and 14B may be depressed to engage one or more internal detents (not shown) with the shaft 72' to secure the expandable catheters 62' in one or more positions.

As shown in FIGS. 2A and 2D, the spring 88 may bias the plunger 86 to the second position (or the spring 88' of FIGS. 14A and 14B may bias the plunger 86' to the second position), where the expandable catheters 62 are in the expanded configuration. The bias of the spring 88 may be overcome by directing the plunger 86 to the first position and then engaging the locking pin 82 (or the locking button 82' shown in FIGS. 14A and 14B) to lock the plunger 86 in the first position, as shown in FIGS. 1A and 1D. Optionally, the locking pin 82 may be engaged in the second position (or any other intermediate position, if desired), e.g., to prevent inadvertent collapse of the expandable catheters 62 once the expandable portions 62c are expanded during use.

In addition, if desired, the balloon 90 may be provided on the proximal portion 52 of the applicator 50, e.g., adjacent the hub 66. As shown, the balloon 90 includes proximal and distal ends 92, 94 mounted around the shaft 72 and tubular extensions 74, e.g., with the distal end 94 immediately adjacent the hub 66. The ends 92, 94 of the balloon 90 may be attached directly around the shaft 72 and/or tubular extensions 74. Alternatively, the ends 92, 94 may be mounted around a collar or other support (not shown) attached around the shaft 72 and/or tubular extensions 74. Such a collar or support may be formed to fit snugly around the shaft 72 and/or tubular extensions 74, e.g., attached thereto by bonding with adhesive, sonic welding, fusing, interference fit, and the like. For example, the ends 92, 94 of the balloon 90 may be attached to the shaft 72 and/or tubular extensions 74 to provide a substantially fluid tight seal between the ends 92, 94, thereby substantially isolating the interior of the balloon 90.

A length of tubing 96 may extend from the balloon 90, e.g., from the proximal end 92 and include a connector 98, e.g., a Luer fitting, for coupling a source of inflation media, e.g., a syringe or other container of saline, air, nitrogen, and the like (not shown). Thus, the source of inflation media may be connected to the fitting 98 and used to deliver inflation media through the tubing 96 into the interior of the balloon 90 to expand the balloon 90 and/or used to aspirate fluid from the interior to collapse the balloon 90.

The balloon 90 may be formed from elastic material, e.g., to provide a compliant or semi-compliant balloon that expands to different sizes depending upon the volume of fluid delivered into the interior of the balloon 90. Alternatively, the balloon 90 may be formed from substantially inelastic material, e.g., to provide a substantially non-compliant balloon that expands to a predetermined size once sufficient fluid is delivered into the interior.

During use, the applicator 50 may be provided with the actuator 80 in the proximal position and the expandable catheters 62 in the expanded configuration, as shown in FIGS. 2A-2D. Immediately before use, the actuator 80 may be directed to and locked in the first or distal position, thereby collapsing the expandable catheters 62 to the collapsed configuration, as shown in FIGS. 1A-1D. Alternatively, the applicator 50 may be provided with the expandable catheters 62 already in the collapsed configuration, e.g., locked (or without the spring 88 biasing the applicator 50 to the second position).

Figure 3B:
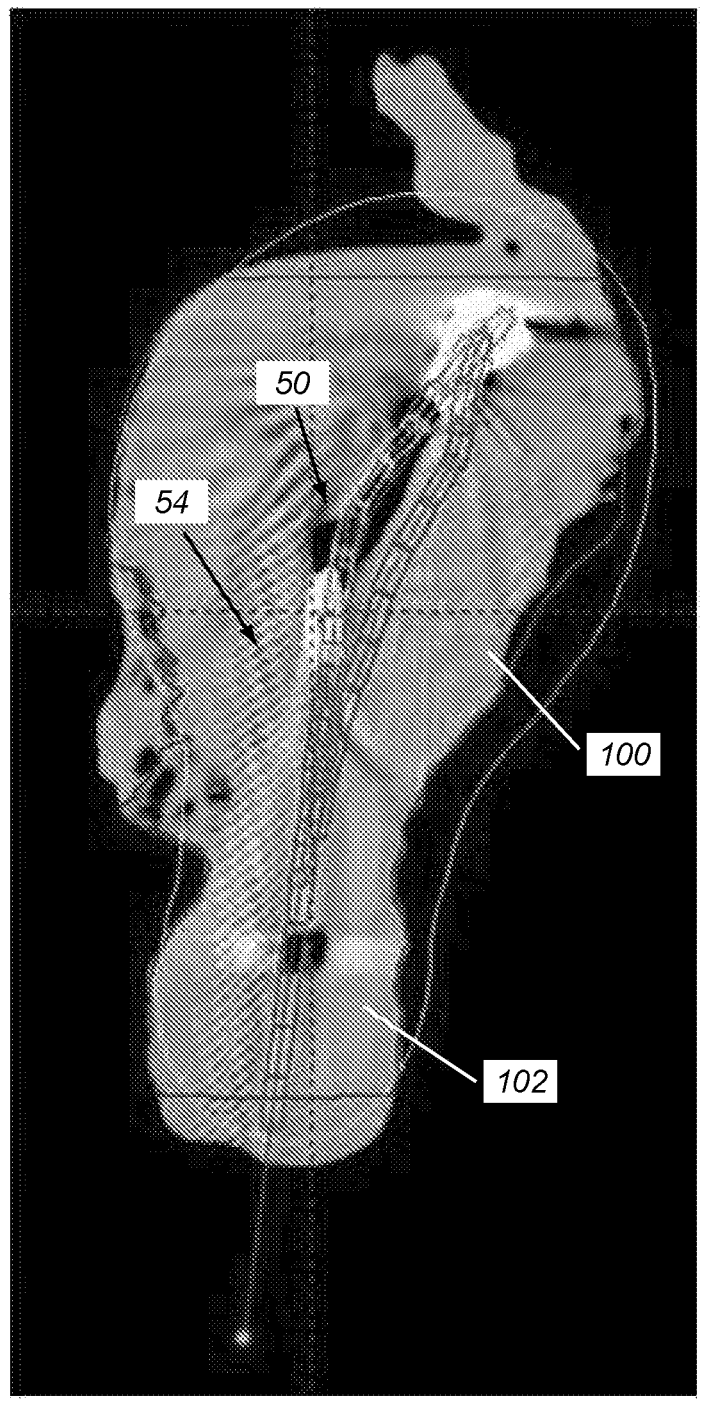
FIG. 3B is another x-ray image taken laterally of the patient's body showing the applicator of FIGS. 1A-2D expanded within the patient's uterus and including isodose profiles superimposed onto the image.

With the expandable catheters 62 in the collapsed configuration, the distal portion 54 of the applicator 50 may be introduced into a vaginal cavity, a lumpectomy cavity, or other target tissue region, e.g., into a uterus 100, as shown in FIGS. 3A and 3B. In an exemplary embodiment, the applicator 50 may be inserted into a vaginal cavity 102 until the distal portion 54 is positioned within the uterus 100. Alternatively, the applicator 50 may be introduced into the vaginal canal 102 until the distal tip 68 is positioned within the external os of the cervix (not shown), e.g., similar to the apparatus and methods disclosed in application Ser. No. 12/543,463, incorporated by reference herein. Optionally, the applicator 50 may be introduced with or through an access device (not shown), similar to embodiments disclosed in the applications incorporated by reference elsewhere herein.

In addition, the applicator 50 may be manipulated to orient the expandable catheters 62 in a desired orientation. For example, it may be desirable to orient the expandable catheters 62 towards the cervix and/or vaginal wall and/or away from the rectum or other regions of the target tissue region. For example, as best seen in FIG. 3B, the applicator 50 may be rotated or otherwise manipulated to align the bend of the distal portion 54 along the natural curve of the uterus 100. In addition, the applicator 50 may be rotated or otherwise manipulated to orient the expandable catheters 62 away from the rectum, i.e., with the center catheter 64 disposed between the expandable catheters 62 and the rectum (not shown). Thus, the plane of expansion of the expandable portions 62c of the expandable catheters 62 may be oriented laterally relative to the patient's body and not anteriorly or posteriorly, as best seen in FIG. 3A.

With the applicator 50 oriented in a desired manner, the expandable portions 62c of the catheters 62 may be directed to the expanded configuration, as shown in FIGS. 2A-2D and FIGS. 3A-3B. If the locking pin 82 of the actuator 80 is locking the plunger 86 in the first or distal position (with the expandable portions 62c in the collapsed configuration), the applicator 50 may be actuated simply by releasing the locking pin 82. Once released, the spring 88 may then bias the plunger 86 and consequently the center catheter 64 to move proximally relative to the expandable catheters 62 to axially compress and expand the expandable portions 62c. Alternatively, the spring 88 may bias the handle 84, shaft 72, and hub 66 to move distally upon release, thereby directing the proximal ends 62b of the expandable catheters 62 distally to expand the expandable portions 62c. Thus, in this alternative, the distal tip 68 of the applicator 50 may remain substantially stationary, e.g., within the os of the cervix if the applicator 50 is merely introduced into the vaginal cavity, which may facilitate stabilization of the applicator 50 during use.

Alternatively, the actuator 80 may be manually directed proximally to the second or proximal position to expand the expandable catheters 62, e.g., if the actuator 80 isn't biased to the second or proximal position. In addition or alternatively, if desired, the locking pin 82 may be engaged in the second position to secure the expandable catheters 62 in the expanded configuration.

With additional reference to FIGS. 2A-2D, once the applicator 50 is properly positioned and the expandable catheters 62 expanded, the balloon 90 may be inflated, e.g., to secure the applicator 50 in position. For example, a syringe (not shown) may be connected to the fitting 98 and fluid delivered into the interior of the balloon 90 to expand the balloon 90 sufficiently to engage tissue surrounding the balloon 90 adjacent the vaginal canal. Thus, with the balloon 90 expanded, the applicator 50 may be substantially stabilized and/or secured within the uterus 100 and/or vaginal cavity 102. In addition, with the balloon 90 expanded, the tubular extensions 74, 76 may pass substantially through a center of the balloon interior, e.g., thereby spacing the extensions 74, 76 away from the surrounding tissue.

As shown in FIGS. 2A-2D, the expandable catheters 62 may extend substantially parallel to the center catheter 64 in the expanded configuration. Alternatively, as shown in FIG. 14B, the expandable catheters 62' may define a different radius of curvature than the bend 64c' of the center catheter 64', e.g., such that the catheters 62', 64' provide multiple curved planes for delivering radiation to surrounding tissue. For example, the curvature of a curved plane within which the expandable catheters 62' lie may have a larger radius of curvature than the bend 64c' of the center catheter 64', e.g. such that midpoints of the catheters 62' are offset laterally from the center catheter 64' by a distance "d." In an exemplary embodiment, the distance "d" of lateral offset may be between about 0.1 and 1.5 centimeters (0.1-1.5 cm). This offset may provide enhanced target tissue coverage during radiation delivery and/or may reduce exposure to healthy or otherwise untargeted tissue.

Returning to FIGS. 2A-2D, with the applicator 50 (or alternatively 50') in the expanded configurations, radiation may be delivered to tissue adjacent the catheters 62, 64, e.g., to the cervix and/or the uterine wall adjacent to the vaginal cavity. For example, the lumens of the catheters 62, 64 may define pathways for receiving radiation source(s). Thus, one or more radiation sources (not shown) may be directed into the openings 75, 77 and lumens of the tubular extensions 74, 76 into the lumens of the catheters 62, 64 to deliver radiation to the tissue surrounding the cavity, e.g., in accordance with a desired dose plan. For example, a HDR radiation source may be introduced sequentially into each of the catheters 62, 64 and held at one or more positions within the distal portion 54 of the applicator 50 to deliver radiation to tissue surrounding the cavity, e.g., as disclosed in the applications incorporated by reference elsewhere herein. With the balloon 90 expanded, radiation source(s) passing through the proximal portion 52 of the applicator 50 may be spaced away from surrounding tissue proximal to the distal portion 54 as the source(s) pass through the balloon 90, which may minimize exposure of otherwise healthy tissue proximal to the target treatment region.

Once sufficient radiation treatment is performed, the applicator 50 may be returned to the collapsed configuration, e.g., by advancing the plunger 86 and then engaging the locking pin 82 in the first or distal position. The collapsed applicator 50 may then be removed from the uterus 100, vaginal cavity 102, and patient's body. If an access device (not shown) remains within the vaginal cavity 102, another applicator (or the same applicator) may be introduced using the access device for one or more subsequent treatments, or the access device may also be removed.

The apparatus and methods described herein may include one or more features similar to those disclosed in co-pending applications Ser. Nos. 10/658,518, filed Sep. 9, 2003 and published as U.S. Publication No. 2004/0116767, Ser. No. 11/276,851, filed Mar. 16, 2006 and published as U.S. Publication No. 2007/0106108, Ser. No. 11/554,731, filed Oct. 31, 2006 and published as U.S. Publication No. 2007/167664, Ser. No. 11/557,747, filed Nov. 8, 2006 and published as U.S. Publication No. 2007/167665, Ser. No. 11/757,231, filed Jun. 1, 2007 and published as U.S. Publication No. 2008/0221384, Ser. No. 11/868,483, filed Oct. 6, 2007 and published as U.S. Publication No. 2008/0091055, 61/014,071 filed Dec. 16, 2007, and Ser. No. 11/266,994, filed Nov. 4, 2005 and published as U.S. Publication No. 2006/0100475. The entire disclosures of these applications are expressly incorporated by reference herein.

For example, optionally, the applicator 50 of FIGS. 1A-2D or 50' of FIGS. 14A and 14B (or any of the applicators in the applications incorporated by reference herein) may include one or more catheter protectors and/or marker devices 180, e.g., removably insertable into the openings 75, 77 and lumens of the tubular extensions 74, 76 and catheters 62, 64, e.g., similar to those disclosed in Ser. No. 11/868,483, incorporated by reference herein. Individual marker devices 180 may be inserted into the lumen of each of the extensions 74, 76, e.g., extending partially into the extensions 74, 76 only within the proximal portion 52 or all the way into the catheters 62, 64 on the distal portion 54.

Figure 4:
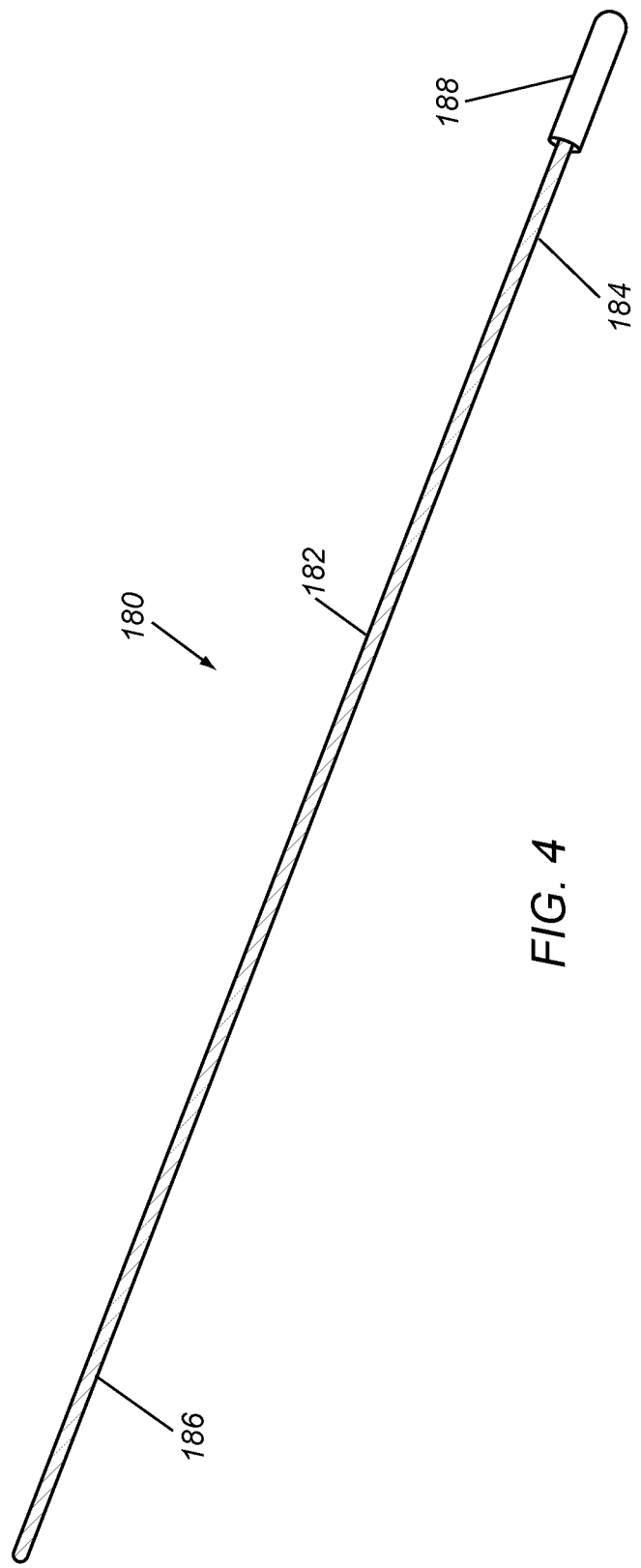
FIG. 4 is a perspective view of an exemplary embodiment of a catheter protector/marker device that may be used with the applicator of FIGS. 1A-2D.

Turning to FIG. 4, an exemplary embodiment of a catheter protector or marker 180 is shown that includes an elongate body, e.g., a plastic-coated (e.g., nylon or FEP) stainless steel solid or tubular member 182, e.g., a monofilament, cable, and the like, including a proximal end 184 and a distal end 186. Optionally, the proximal end 182 may include an end cap 188 for sealing the lumen of an extension 74, 76 (not shown in FIG. 6), as described further below. The marker device 180 may have a length corresponding to the length of the extensions 74, 76 and catheters 62, 64, e.g., such that the cap 188 may engage, cover, or otherwise seal the opening 75, 77 in the extension 74, 76 into which the marker device 180 is fully inserted, while the distal end 186 is positioned within or adjacent the distal tip 68.

The radiopacity and/or other characteristics of the marker device 180 may enhance monitoring the location and/or orientation of the catheters 62, 64, e.g., within a patient's body by identifying the marker devices 180 received therein. For example, the marker devices 180 may delineate the entire path for an HDR catheter, e.g., using x-ray, ultrasound, or other imaging modalities. The distal ends 186 of the marker devices 180 may also be used to help identify an initial dwell position of an HDR source introduced sequentially into the catheters 62, 64 (after removing the marker devices 180).

When a dose plan is optimized, the characteristics of the radioactive sources (e.g., brachytherapy devices) are chosen (e.g., LDR seed activity levels, HDR dwell positions and/or times, etc.), and prepared for placement into the applicator 50 via the openings 75, 77 in the proximal ends 32 of the extensions 74, 76. The marker devices 180 may then be removed before treatment.

The marker devices 180 may also support the extensions 74, 76 and/or catheters 62, 64. For example, a cable or tubular member may provide a relatively strong yet flexible support that may be inserted into the catheters 62, 64 between treatments. Thus, the marker devices 180 may prevent kinking or other deformation or damage to the catheters 62, 64 between treatments, e.g., for HDR therapies.

Optionally, the marker devices 180 may be used to seal the lumens of an extensions 74, 76 and/or catheters 62, 64, e.g., to prevent fluid, debris, and the like from entering. As shown, the marker devices 180 may include an end cap 188 on the proximal end 184, which may be seated over or otherwise seal the proximal ends of the extensions 74, 76.

Turning to FIGS. 5A-10A, alternative embodiments of catheter protectors and/or marker devices are shown that may include one or more features for enhancing imaging of the marker devices and, therefore the applicator within which the marker devices are introduced. For example, FIGS. 5A-5C show a marker device 180A that includes a solid or tubular member 182A including a proximal end 184A with a cap 188A and a distal end 186A sized for introduction into a lumen of a catheter and/or tubular extension. In addition, the marker device 180A includes a distal region 187A including one or more helical grooves 189A extending therealong. The groove(s) 189A may provide echogenic features that enhance imaging the distal portion 187A using ultrasound, e.g., with the marker device 180A placed within a lumen of the applicator 50 described above (or any of the apparatus disclosed in the applications incorporated by reference herein).

FIGS. 6A-6C show another marker device 180B that includes a tubular member 182B including a proximal end 184B with a cap 188B and a distal end 186B sized for introduction into a lumen of a catheter and/or tubular extension. In addition, the marker device 180B includes a distal region 187B including one or more circular or elliptical recesses 189B formed in the outer surface of the distal region 187B.

FIGS. 7A-7C show yet another marker device 180C that includes a tubular member 182C including a proximal end 184C with a cap 188C and a distal end 186C sized for introduction into a lumen of a catheter and/or tubular extension. In addition, the marker device 180C includes a distal region 187C including a plurality of longitudinal grooves 189C formed in the outer surface of the distal region 187C.

FIGS. 8A and 8B show still another marker device 180D that includes a tubular member 182D including a proximal end 184D with a cap 188D and a distal end 186D sized for introduction into a lumen of a catheter and/or tubular extension. As best seen in FIG. 8B, a distal portion 187D of the marker device 180D includes a plurality of seeds 190D separated by spacers 192D. The seeds 190D and spacers 192D are aligned axially with one another and encased within heat shrink tubing 194D or other sleeve. The seeds 190D include a plurality of features, e.g., helical openings and/or ribs and or tapered shapes, that may enhance imaging the seeds 190D using ultrasound imaging. For example, the seeds 190D may be formed from a section of tubing that has material removed to define the features, e.g., by laser cutting, chemical etching, and the like. Alternatively, the seeds 190D may be formed from a sheet that has the features formed therein, e.g., before the sheet is rolled into the tubular shape of the seeds 190D.

FIGS. 9A and 9B show still another marker device 180E including echogenic seeds 190E similar to the seeds 190D except having a substantially uniform diameter between tapered ends. FIGS. 10A and 10B show yet another marker device 180F including echogenic seeds 190F. The seeds 190F in this embodiment include a plurality of diamond features that may enhance imaging using ultrasound.

In addition or alternatively, if desired, one or more markers (not shown) may be provided on the applicator 50 itself, e.g., on the distal tip 68 and/or catheters 62, 64 to facilitate positioning and/or orienting the applicator 50, e.g., using external imaging. In exemplary embodiments, the markers may include radiopaque markers to facilitate imaging using fluoroscopy or CT scan, echogenic markers to facilitate imaging using ultrasound, and the like.

For example, as shown in FIGS. 11A-11C, a tubular body 160A is shown that may include a distal portion 162A and a proximal portion 174A, e.g., which may provide a catheter 62 and tubular extension 74 of the applicator 50 shown in FIGS. 1A-2D (or applicator 50' of FIGS. 14A and 14B). The distal portion 162A includes one or more helical grooves 163A formed in the outer surface thereof, e.g., similar to the marker device 180A described above. FIGS. 12A-12C show an alternative embodiment of a tubular body 160B that includes a plurality of circular and/or elliptical recesses 163B formed in the outer surface of a distal portion 162B. FIGS. 13A-13C show another alternative embodiment of a tubular body 160C that includes a plurality of longitudinal grooves 163C formed in the outer surface of a distal portion 162C. The features may be formed in the outer wall of the tubular body 160A-160C without extending entirely through the wall of the tubular body 160A-160C, e.g., to maintain the integrity of the internal lumen of the tubular body 160A-160C.

Any of these echogenic features may be provided on the entire distal portion of a tubular body or otherwise on catheters 62, 64 of the applicator 50. Alternatively, the catheters 62, 64 of FIGS. 1A-2D may be formed from multiple tubular bodies attached together with one or more of the tubular bodies including echogenic or other features formed in the outer surface thereof. The features may enhance imaging the catheters 62, 64 using ultrasound or other external imaging, as described elsewhere herein.

In addition or alternatively, the support members 70 may include markers and/or may be fabricated to include one or more features to enhance visualization of the support members 70, e.g., using ultrasound, fluoroscopy, CT scan, or other external imaging.

Optionally, the applicator 50 (or 50') may include one or more visual indicators (not shown) to facilitate identifying respective tubular extensions 74, 76 during delivery of radiation source(s) into the catheters 62, 64.

Exemplary embodiments of the present invention are described above. Those skilled in the art will recognize that many embodiments are possible within the scope of the invention. Other variations, modifications, and combinations of the various components and methods described herein can certainly be made and still fall within the scope of the invention. For example, any of the treatment devices described herein may be combined with any of the delivery systems and methods also described herein. Thus, the invention is limited only by the following claims, and equivalents thereto.

We claim:

1. A brachytherapy treatment apparatus, comprising:
an elongate core member comprising proximal and distal ends defining a central longitudinal axis therebetween, the core member comprising a bend between the proximal and distal ends;
a pair of elongate members comprising proximal and distal ends and pathways extending between the elongate member proximal and distal ends for receiving a source of radiation therealong, the elongate member distal ends coupled to the distal end of the core member;
an actuator coupled to the elongate members adjacent expandable distal portions of the elongate members and movable axially relative to the core member for moving the expandable distal portions of the elongate members between a collapsed configuration wherein the expandable distal portions extend substantially parallel to the core member and an expanded configuration wherein the expandable distal portions bow away from one another substantially within a curved plane aligned generally with the bend of the core member; and
an expandable member comprising an expandable member distal end surrounding the elongate members proximal to the expandable distal portions and an expandable member proximal end surrounding the elongate members closer to the elongate member proximal ends than the expandable member distal end.

2. The apparatus of claim 1, wherein the curved plane of the distal portions extends substantially parallel to the core member in the expanded configuration.

3. The apparatus of claim 1, wherein the curved plane of the distal portions defines a radius of curvature that is larger than a radius of curvature defined by the bend of the core member.

4. The apparatus of claim 1, wherein the curved plane of the distal portions is offset from the core member such that a midpoint of the distal portions is offset laterally from the bend of the core member.

5. The apparatus of claim 1, wherein the core member is substantially rigid such that the bend defines a predetermined angle.

6. The apparatus of claim 1, wherein the core member is malleable such that the shape of the bend is adjustable.

7. The apparatus of claim 1, wherein the core member comprises a center catheter having a lumen for receiving a source of radiation therein, and the elongate members comprise expandable catheters including lumens defining the pathways for receiving a source of radiation.

8. The apparatus of claim 1, wherein the actuator comprises a hub fixed to the elongate members proximal to the distal portions and a handle adjacent the elongate member proximal ends that is coupled to the hub.

9. The apparatus of claim 8, wherein the expandable member comprises a balloon and wherein the balloon distal end is located adjacent the hub proximal to the distal portions.

10. The apparatus of claim 8, wherein the actuator further comprises a plunger coupled to the core member that is movable relative to the handle between a distal position in which the distal portions of the elongate members are in the collapsed configuration and a proximal position in which the core member is pulled proximally to cause the distal portions of the elongate members to bow outwardly towards the expanded configuration.

11. The apparatus of claim 1, wherein the elongate members are offset from the core member such that the curved plane does not intersect the core member.

12. The apparatus of claim 1, wherein the elongate members are offset from the core member such that the curved plan intersects the central longitudinal axis from a lateral view at one or more locations.

13. The apparatus of claim 1, further comprising a third elongate member comprising a proximal end, a distal end coupled to the core member distal end, and a pathway for receiving a source of radiation therealong, the actuator coupled to the third elongate member adjacent a distal portion of the third elongate member such that, when the actuator is moved axially relative to the core member, the distal portion of the third elongate member is also directed between a collapsed configuration wherein the distal portion extends substantially parallel to the core member and an expanded configuration wherein the distal portion bows away from the core member out of the plane defined by the pair of elongate members.

14. A brachytherapy treatment apparatus for treating tissue adjacent a vaginal cavity, comprising:
   an elongate core member comprising proximal and distal ends defining a central longitudinal axis therebetween, the core member comprising a substantially rigid body having a bend between the proximal and distal ends;
   a distal tip coupled to the core member distal end sized to be received in an external os of a cervix;
   a plurality of tubular members comprising proximal and distal ends and lumens extending between the tubular member proximal and distal ends for receiving a source of radiation therealong, the tubular member distal ends coupled to the distal tip, the tubular members comprising expandable distal portions extending along the core member adjacent the bend;
   a hub coupled to the tubular members proximal the distal tip and movable relative to the core member; and
   an actuator coupled to the hub and the core member proximal end for moving the expandable distal portions of the tubular members between the hub and distal tip between a collapsed configuration wherein the expandable distal portions extend substantially parallel to the core member and an expanded configuration wherein the expandable distal portions bow away from one another substantially within a curved plane aligned generally with the bend of the core member.

15. The apparatus of claim 14, further comprising an expandable member including a distal end adjacent the hub proximal to the distal portions and surrounding proximal portions of the tubular members proximal to the expandable distal portions.

16. The apparatus of claim 14, wherein the tubular members are disposed adjacent the core member on one side of the curved plane in the expanded configuration.

17. The apparatus of claim 14, wherein the plurality of tubular members consists of two elongate members.

18. The apparatus of claim 14, wherein the core member comprises a center catheter having a lumen for receiving a source of radiation therein.

19. The apparatus of claim 14, wherein the curved plane of the distal portions extends substantially parallel to the core member in the expanded configuration.

20. The apparatus of claim 14, wherein the curved plane of the distal portions defines a radius of curvature that is larger than a radius of curvature defined by the bend of the core member.

21. The apparatus of claim 14, wherein the curved plane of the distal portions is offset from the core member such that a midpoint of the distal portions is offset laterally from the bend of the core member.

22. A brachytherapy treatment apparatus, comprising:
   an elongate core member comprising proximal and distal ends defining a central longitudinal axis therebetween;
   a plurality of elongate members comprising proximal and distal ends and pathways extending between the elongate member proximal and distal ends for receiving a source of radiation therealong, the elongate member distal ends coupled to the distal end of the core member;
   an actuator coupled to the elongate members proximal to expandable distal portions of the elongate members and movable axially relative to the core member for moving the expandable distal portions of the elongate members between a collapsed configuration wherein the expandable distal portions extend substantially parallel to the core member and an expanded configuration wherein the distal portions bow away from one another; and
   an expandable member comprising an expandable member distal end surrounding the elongate members proximal to the expandable distal portions and an expandable member proximal end surrounding of the elongate members closer to the elongate member proximal ends than the expandable member distal end.

23. The apparatus of claim 22, further comprising a hub fixed to the elongate members adjacent the distal portions, the actuator comprising:
   a handle coupled to the hub; and
   a plunger coupled to the core member that is movable relative to the handle between a distal position in which the distal portions of the elongate members are in the collapsed configuration and a proximal position in which the core member is pulled proximally to cause the distal portions of the elongate members to bow outwardly towards the expanded configuration.

24. The apparatus of claim 22, wherein the expandable member comprises a balloon located adjacent the hub proximal to the distal portions.

* * * * *